US005712248A

United States Patent [19]

Kalman et al.

[11] Patent Number: 5,712,248
[45] Date of Patent: Jan. 27, 1998

[54] METHOD OF CONTROLLING INSECT WITH NOVEL INSECTICIDAL PROTEIN

[75] Inventors: Sue S. Kalman, Saratoga; Kristine L. Kiehne, San Jose, both of Calif.

[73] Assignee: Sandoz LTD., Basel, Switzerland

[21] Appl. No.: 434,823

[22] Filed: May 4, 1995

Related U.S. Application Data

[62] Division of Ser. No. 197,998, Feb. 16, 1994, abandoned, which is a continuation of Ser. No. 102,316, Aug. 5, 1993, abandoned, which is a continuation of Ser. No. 4,474, Jan. 14, 1993, abandoned, which is a continuation of Ser. No. 844,302, Feb. 27, 1992, abandoned.

[51] Int. Cl.[6] ........................... A01N 37/18; A01N 63/00

[52] U.S. Cl. ........................................ 514/12; 424/93.461

[58] Field of Search ...................... 530/350; 424/93.461; 514/12

[56] References Cited

U.S. PATENT DOCUMENTS 5,164,180 11/1992 Payne et al. ....................... 424/94.461

FOREIGN PATENT DOCUMENTS 0 401 979 12/1990 European Pat. Off. .

OTHER PUBLICATIONS

Chestukhina et al. *Bacillus thuringiensis* ssp. galleriae simultaneously produces two delta endotoxins differing strongly in primary structure and entomocidal activity. FEBS Letters 232 (1):249–251., May 1988.

Smulevitch et al. Nucleotide sequence of a novel delta endotoxin gene crylg of *Bacillus thuringiensis* ssp. galleriae. FEBS Letters 293(1,2): 25–28. Nov. 1991.

Bowie et al. Deciphering the message in protein sequences: tolerance to amino acid substitutions. Science 247:1306–1310. , Mar. 1990.

Schnepf, H. et al. 1985 "Amino Acid Sequence of a Crystal Protein from *Bacillus thuringiensis* Deducted . . . "J. Biol. Chem. 260:6264–6272.

Honee, G. et al. 1985 "Nucleotide Sequence of Crystal Protein Gene Isolated from *B. thuringiensis* subspecies . . . "Nucl. Acids Res. 16 (13) : 6240.

Hofte, H. et al. 1990 "Nucleotide Sequence and Deduced Amion Acid Sequence of a New Lepidoptera–Specific . . . "Nucl. Acids Res. 18(18): 5545.

Hofte, H. et al. 1986 "Structure and Functional Analysis of a Cloned Delta Endotoxin of *B. thuringiensis* berliner "Eur. J. Biochem. 161:273–280.

Visser, B. et al. 1990 A Novel *Bacillus thuringiensis* Gene Encoding a Spodoptera extiguq–Specific Crystal Protein J. Bact. 172(12):6783–6788.0

Adang M. et al. 1985 "Characterized Full–Length and Truncated Plasmid Clones of a Crystal Protein . . . "Gene 36:289–300.

Brizzard, B. et al. 1988 "Nucleotide sequence of an additional Crystal Protein Gene Cloned . . . "Nucl. Acids Res. 16(6):2723.

Prefontaine, G. et al., 1987 "Use of Oligonucleotide Probes to Study the Relatedness of Delta–Endotoxin..."Applied & Environ. Micro. 53:2808–2814.

Haider, M. et al. 1987 "Cloning and Heterologous Expression of an Insecticidal Delta–Endotoxin Gene . . . "Gene 52:285–290.

*Primary Examiner*—Robert A. Wax
*Assistant Examiner*—G. E. Bugaisky
*Attorney, Agent, or Firm*—Lynn Marcus-Wyner; Michael P. Morris

[57] ABSTRACT

A novel insecticidal protein isolated from *Bacillus thuringiensis* var. *galleria* is described and its DNA sequence is given. This protein, called CryIC(b), is toxic to Lepidoptera, including Spodoptera.

8 Claims, 3 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 4106 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 296..3826
        ( D ) OTHER INFORMATION: /codon_start= 296

( x i ) SEQUENCE DESCRIPTION: SEQ ID NO:1:

```
TAGATTTTAT    ATAAGTATAA    AAAATAATAA    GACTTTAATA    TAAGTTAAGG    GAATACAAAT        60

CCTTAATGCA    TTGGTTAAAT    ATTATAAACT    CTAAAGCATG    GATGATGGTT    GAGAAGTAAG       120

TAGATTATTA    ACACCCTGGG    TCTATTTTAG    CCCCAGGGTA    TAAATTGATA    TTTAATAAAA       180

TCGGTTGCAC    TTTGAGTATT    TTTTCATAGA    ATGACTCATA    TGATTAACAT    TGCAATACAG       240

TAAAAGATCT    TTAGTTATAA    AGAAAAACTA    TTACGCTAAA    AAGTGGAGGG    AACAT ATG       298
                                                                           Met
                                                                            1

GAG    AAT    AAT    ATT    CAA    AAT    CAA    TGC    GTA    CCT    TAC    AAT    TGT    TTA    AGT    AAT        346
Glu    Asn    Asn    Ile    Gln    Asn    Gln    Cys    Val    Pro    Tyr    Asn    Cys    Leu    Ser    Asn
                      5                        10                              15

CCT    GAG    GAG    ATA    CTT    TTA    GAT    GGA    GAA    AGA    ATA    TCA    ACT    GGT    AAT    TCA        394
Pro    Glu    Glu    Ile    Leu    Leu    Asp    Gly    Glu    Arg    Ile    Ser    Thr    Gly    Asn    Ser
              20                              25                              30

TCA    ATT    GAT    ATC    TCT    CTG    TCA    CTT    GTC    CAG    CTT    CTG    GTA    TCT    AAC    TTT        442
Ser    Ile    Asp    Ile    Ser    Leu    Ser    Leu    Val    Gln    Leu    Leu    Val    Ser    Asn    Phe
         35                              40                              45
```

-continued

| | | | | | | | | | | | | | | | |
|---|---|---|---|---|---|---|---|---|---|---|---|---|---|---|---|
| GTA | CCA | GGG | GGA | GGA | TTT | TTA | GTT | GGA | TTA | TTA | GAT | TTT | GTA | TGG | GGA |
| Val | Pro | Gly | Gly | Gly | Phe | Leu | Val | Gly | Leu | Leu | Asp | Phe | Val | Trp | Gly |
| 50 | | | | | 55 | | | | | 60 | | | | | 65 |

490

| ATA | GTA | GGC | CCT | TCT | CCA | TGG | GAT | GCA | TTT | CTA | GTG | CAA | ATT | GAA | CAA |
|---|---|---|---|---|---|---|---|---|---|---|---|---|---|---|---|
| Ile | Val | Gly | Pro | Ser | Pro | Trp | Asp | Ala | Phe | Leu | Val | Gln | Ile | Glu | Gln |
| | | | | 70 | | | | | 75 | | | | | 80 | |

538

| TTA | ATT | AAT | GAA | AGA | ATA | GCT | GCA | TAT | GCT | AGG | TCT | GCA | GCA | ATT | TCT |
|---|---|---|---|---|---|---|---|---|---|---|---|---|---|---|---|
| Leu | Ile | Asn | Glu | Arg | Ile | Ala | Ala | Tyr | Ala | Arg | Ser | Ala | Ala | Ile | Ser |
| | | | | 85 | | | | | 90 | | | | | 95 | |

586

| AAT | TTA | GAA | GGA | TTA | GGA | AAC | AAT | TTC | AAT | ATA | TAT | GTG | GAA | GCA | TTT |
|---|---|---|---|---|---|---|---|---|---|---|---|---|---|---|---|
| Asn | Leu | Glu | Gly | Leu | Gly | Asn | Asn | Phe | Asn | Ile | Tyr | Val | Glu | Ala | Phe |
| | | | | 100 | | | | | 105 | | | | | 110 | |

634

| AAA | GAA | TGG | GAA | GCA | GAT | CCT | GAT | AAT | CCA | GTA | ACC | AGG | ACT | AGA | GTA |
|---|---|---|---|---|---|---|---|---|---|---|---|---|---|---|---|
| Lys | Glu | Trp | Glu | Ala | Asp | Pro | Asp | Asn | Pro | Val | Thr | Arg | Thr | Arg | Val |
| | | 115 | | | | | 120 | | | | | 125 | | | |

682

| GTT | GAT | CGC | TTT | CGT | ATA | CTT | GAT | GGG | CTA | CTT | GAA | AGG | GAC | ATC | CCT |
|---|---|---|---|---|---|---|---|---|---|---|---|---|---|---|---|
| Val | Asp | Arg | Phe | Arg | Ile | Leu | Asp | Gly | Leu | Leu | Glu | Arg | Asp | Ile | Pro |
| 130 | | | | | 135 | | | | | 140 | | | | | 145 |

730

| TCA | TTT | CGA | ATT | GCT | GGA | TTT | GAA | GTA | CCC | CTT | TTA | TCC | GTT | TAT | GCT |
|---|---|---|---|---|---|---|---|---|---|---|---|---|---|---|---|
| Ser | Phe | Arg | Ile | Ala | Gly | Phe | Glu | Val | Pro | Leu | Leu | Ser | Val | Tyr | Ala |
| | | | | 150 | | | | | 155 | | | | | 160 | |

778

| CAA | GCG | GCC | AAT | TTG | CAT | CTA | GCT | ATA | TTA | AGA | GAT | TCT | TCA | ATT | TTT |
|---|---|---|---|---|---|---|---|---|---|---|---|---|---|---|---|
| Gln | Ala | Ala | Asn | Leu | His | Leu | Ala | Ile | Leu | Arg | Asp | Ser | Ser | Ile | Phe |
| | | | | 165 | | | | | 170 | | | | | 175 | |

826

| GGA | GCA | AGA | TGG | GGA | TTG | ACA | ACA | ATA | AAT | GTC | AAT | GAA | AAC | TAT | AAT |
|---|---|---|---|---|---|---|---|---|---|---|---|---|---|---|---|
| Gly | Ala | Arg | Trp | Gly | Leu | Thr | Thr | Ile | Asn | Val | Asn | Glu | Asn | Tyr | Asn |
| | | | 180 | | | | | 185 | | | | | 190 | | |

874

| AGG | CTA | ATT | AGG | CAT | ATT | GAT | GAA | TAT | GCT | AAT | CAC | TGT | GCA | GAT | ACG |
|---|---|---|---|---|---|---|---|---|---|---|---|---|---|---|---|
| Arg | Leu | Ile | Arg | His | Ile | Asp | Glu | Tyr | Ala | Asn | His | Cys | Ala | Asp | Thr |
| | | 195 | | | | | 200 | | | | | 205 | | | |

922

| TAT | AAT | CGG | GGA | TTA | AAT | AAT | TTA | CCA | AAA | TCT | ACG | TAT | CAA | GAT | TGG |
|---|---|---|---|---|---|---|---|---|---|---|---|---|---|---|---|
| Tyr | Asn | Arg | Gly | Leu | Asn | Asn | Leu | Pro | Lys | Ser | Thr | Tyr | Gln | Asp | Trp |
| 210 | | | | | 215 | | | | | 220 | | | | | 225 |

970

| ATA | ACA | TAT | AAT | CGA | TTA | CGG | AGA | GAC | TTA | ACA | TTA | ACT | GTA | TTA | GAT |
|---|---|---|---|---|---|---|---|---|---|---|---|---|---|---|---|
| Ile | Thr | Tyr | Asn | Arg | Leu | Arg | Arg | Asp | Leu | Thr | Leu | Thr | Val | Leu | Asp |
| | | | | 230 | | | | | 235 | | | | | 240 | |

1018

| ATC | GCT | GCT | TTC | TTT | CCA | AGC | TAT | GAC | AAT | AGG | AGA | TAT | CCA | ATT | CAG |
|---|---|---|---|---|---|---|---|---|---|---|---|---|---|---|---|
| Ile | Ala | Ala | Phe | Phe | Pro | Ser | Tyr | Asp | Asn | Arg | Arg | Tyr | Pro | Ile | Gln |
| | | | | 245 | | | | | 250 | | | | | 255 | |

1066

| TCA | GTT | GGT | CAA | CTA | ACA | AGG | GAA | ATT | TAT | ACG | GAC | CCA | TTA | ATT | ACT |
|---|---|---|---|---|---|---|---|---|---|---|---|---|---|---|---|
| Ser | Val | Gly | Gln | Leu | Thr | Arg | Glu | Ile | Tyr | Thr | Asp | Pro | Leu | Ile | Thr |
| | | 260 | | | | | 265 | | | | | 270 | | | |

1114

| TTT | AAT | CCA | CAG | TTA | CAG | TCT | GTA | GCT | CAA | TTA | CCT | ACT | TTT | AAC | GTT |
|---|---|---|---|---|---|---|---|---|---|---|---|---|---|---|---|
| Phe | Asn | Pro | Gln | Leu | Gln | Ser | Val | Ala | Gln | Leu | Pro | Thr | Phe | Asn | Val |
| | | 275 | | | | | 280 | | | | | 285 | | | |

1162

| ATG | GAA | AGC | AAC | GCA | ATT | AGA | ACT | CCT | CAT | TTA | TTT | GAT | GTA | TTG | AAT |
|---|---|---|---|---|---|---|---|---|---|---|---|---|---|---|---|
| Met | Glu | Ser | Asn | Ala | Ile | Arg | Thr | Pro | His | Leu | Phe | Asp | Val | Leu | Asn |
| 290 | | | | | 295 | | | | | 300 | | | | | 305 |

1210

| AAT | CTT | ACA | ATT | TTT | ACA | GAT | TGG | TTT | AGT | GTT | GGA | CGC | AAC | TTT | TAT |
|---|---|---|---|---|---|---|---|---|---|---|---|---|---|---|---|
| Asn | Leu | Thr | Ile | Phe | Thr | Asp | Trp | Phe | Ser | Val | Gly | Arg | Asn | Phe | Tyr |
| | | | | 310 | | | | | 315 | | | | | 320 | |

1258

| TGG | GGA | GGA | CAT | CGA | GTA | ATA | TCT | AAC | CGT | ATA | GGA | GGA | GGT | AAC | ATA |
|---|---|---|---|---|---|---|---|---|---|---|---|---|---|---|---|
| Trp | Gly | Gly | His | Arg | Val | Ile | Ser | Asn | Arg | Ile | Gly | Gly | Gly | Asn | Ile |
| | | | 325 | | | | | 330 | | | | | 335 | | |

1306

| ACA | TCT | CCT | ATA | TAT | GGA | AGA | GAG | GCG | AAT | CAG | GAG | CCT | CCA | AGA | TCT |
|---|---|---|---|---|---|---|---|---|---|---|---|---|---|---|---|
| Thr | Ser | Pro | Ile | Tyr | Gly | Arg | Glu | Ala | Asn | Gln | Glu | Pro | Pro | Arg | Ser |
| | | | 340 | | | | | 345 | | | | | 350 | | |

1354

| TTT | ACT | TTT | AAT | GGG | CCT | GTT | TTT | AGG | ACT | TTA | TCA | AAT | CCT | ACT | TTT |
|---|---|---|---|---|---|---|---|---|---|---|---|---|---|---|---|
| Phe | Thr | Phe | Asn | Gly | Pro | Val | Phe | Arg | Thr | Leu | Ser | Asn | Pro | Thr | Phe |
| | | 355 | | | | | 360 | | | | | 365 | | | |

1402

| | | | | | | | | | | | | | | | | |
|---|---|---|---|---|---|---|---|---|---|---|---|---|---|---|---|---|
| AGA | CCT | TTA | CAG | CAA | CCT | TGG | CCA | GCG | CCA | CCA | TTT | AAT | TTA | CGT | GGT | 1450 |
| Arg 370 | Pro | Leu | Gln | Gln 375 | Pro | Trp | Pro | Ala | Pro 380 | Pro | Phe | Asn | Leu | Arg | Gly 385 | |
| GTT | GAA | GGA | GTA | GAA | TTT | TCT | ACA | CCT | TTA | AAT | AGC | TTT | ACG | TAT | CGA | 1498 |
| Val | Glu | Gly | Val | Glu 390 | Phe | Ser | Thr | Pro | Leu 395 | Asn | Ser | Phe | Thr | Tyr 400 | Arg | |
| GGA | AGA | GGT | ACG | GTT | GAT | TCT | TTA | ACT | GAG | TTA | CCG | CCT | GAG | GAT | AAT | 1546 |
| Gly | Arg | Gly | Thr 405 | Val | Asp | Ser | Leu | Thr 410 | Glu | Leu | Pro | Pro | Glu 415 | Asp | Asn | |
| AGT | GTG | CCT | CCT | CGC | GAA | GGA | TAT | AGT | CAT | CGT | TTA | TGT | CAT | GCA | ACT | 1594 |
| Ser | Val | Pro 420 | Pro | Arg | Glu | Gly | Tyr 425 | Ser | His | Arg | Leu 430 | Cys | His | Ala | Thr | |
| TTT | GTT | CAA | AGA | TCT | GGA | ACC | CCA | TTT | TTA | ACA | ACT | GGT | CCA | GTA | TTT | 1642 |
| Phe | Val 435 | Gln | Arg | Ser | Gly | Thr 440 | Pro | Phe | Leu | Thr | Thr 445 | Gly | Pro | Val | Phe | |
| TCT | TGG | ACG | CAT | CGT | AGT | GCT | ACT | GAT | CGA | AAT | ATA | ATC | TAC | CCG | GAT | 1690 |
| Ser Trp 450 | Trp | Thr | His | Arg | Ser 455 | Ala | Thr | Asp | Arg | Asn 460 | Ile | Ile | Tyr | Pro | Asp 465 | |
| GTA | ATT | AAC | CAA | ATA | CCG | TTA | GTA | AAA | GCA | TTC | AAC | CTT | ACT | TCA | GGT | 1738 |
| Val | Ile | Asn | Gln | Ile 470 | Pro | Leu | Val | Lys | Ala 475 | Phe | Asn | Leu | Thr | Ser 480 | Gly | |
| ACC | TCT | GTA | GTC | AGA | GGT | CCA | GGA | TTT | ACA | GGA | GGG | GAT | ATC | ATC | CGA | 1786 |
| Thr | Ser | Val | Val 485 | Arg | Gly | Pro | Gly | Phe 490 | Thr | Gly | Gly | Asp | Ile 495 | Ile | Arg | |
| ACT | AAC | GTT | AAT | GGT | AGT | GTA | CTA | AGT | ATG | AGT | CTT | AAT | TTT | AGT | AAC | 1834 |
| Thr | Asn | Val 500 | Asn | Gly | Ser | Val | Leu 505 | Ser | Met | Ser | Leu | Asn 510 | Phe | Ser | Asn | |
| ACA | ACA | TTA | CAG | CGG | TAT | CGT | GTG | AGA | GTT | CGT | TAT | GCT | GCT | TCT | CAA | 1882 |
| Thr | Thr | Leu 515 | Gln | Arg | Tyr | Arg | Val 520 | Arg | Val | Arg | Tyr | Ala 525 | Ala | Ser | Gln | |
| ACA | ATG | GTC | ATG | AGC | GTA | ACT | GTT | GGA | GGG | AGT | ACT | ACT | GGT | AAT | CAA | 1930 |
| Thr 530 | Met | Val | Met | Ser | Val 535 | Thr | Val | Gly | Gly | Ser 540 | Thr | Thr | Gly | Asn | Gln 545 | |
| GGA | TTC | CCT | AGT | ACT | ATG | AGT | GCA | AAT | GGG | GCT | TTG | ACA | TCT | CAA | TCA | 1978 |
| Gly | Phe | Pro | Ser 550 | Thr | Met | Ser | Ala | Asn 555 | Gly | Ala | Leu | Thr | Ser 560 | Gln | Ser | |
| TTT | AGA | TTC | GCA | GAA | TTT | CCT | GTA | GGT | ATT | AGT | GCA | TCT | GGC | AGT | CAA | 2026 |
| Phe | Arg | Phe | Ala 565 | Glu | Phe | Pro | Val | Gly 570 | Ile | Ser | Ala | Ser | Gly 575 | Ser | Gln | |
| GGT | GCA | TCA | ATA | AGT | ATT | AGT | AAT | AAT | GTA | GGT | AGA | CAA | ATG | TTT | CAC | 2074 |
| Gly | Ala | Ser | Ile 580 | Ser | Ile | Ser | Asn | Asn 585 | Val | Gly | Arg | Gln | Met 590 | Phe | His | |
| TTA | GAT | AGA | ATT | GAA | TTT | CTC | CCA | GTT | ACT | TCT | ACA | TTT | GAG | GAG | GAA | 2122 |
| Leu | Asp 595 | Arg | Ile | Glu | Phe | Leu 600 | Pro | Val | Thr | Ser | Thr 605 | Phe | Glu | Glu | Glu | |
| TAT | GAT | TTA | GAA | AGA | GCG | CAA | GAG | GCG | GTG | AAT | GCC | CTG | TTT | ACT | TCT | 2170 |
| Tyr 610 | Asp | Leu | Glu | Arg | Ala 615 | Gln | Glu | Ala | Val | Asn 620 | Ala | Leu | Phe | Thr | Ser 625 | |
| ACG | AAC | CAA | CTA | GGG | CTA | AAA | ACA | GAT | GTA | ACG | GAT | TAT | CAT | ATT | GAT | 2218 |
| Thr | Asn | Gln | Leu | Gly 630 | Leu | Lys | Thr | Asp | Val 635 | Thr | Asp | Tyr | His | Ile 640 | Asp | |
| CAA | GTA | TCA | AAT | CTA | GTT | GAA | TGC | TTA | TCG | GAT | GAA | TTT | TGT | CTG | GAT | 2266 |
| Gln | Val | Ser | Asn 645 | Leu | Val | Glu | Cys | Leu 650 | Ser | Asp | Glu | Phe | Cys 655 | Leu | Asp | |
| GAA | AAG | CGA | GAA | TTG | TCT | GAG | AAA | GTC | AAA | CAT | GCG | AAG | CGA | CTC | AGC | 2314 |
| Glu | Lys | Arg 660 | Glu | Leu | Ser | Glu | Lys 665 | Val | Lys | His | Ala | Lys 670 | Arg | Leu | Ser | |
| GAT | GAG | CGC | AAT | TTA | CTC | CAG | GAT | CGA | AAT | TTC | AGA | TCC | ATT | AAT | GGG | 2362 |
| Asp | Glu | Arg | Asn 675 | Leu | Leu | Gln | Asp | Arg 680 | Asn | Phe | Arg | Ser | Ile 685 | Asn | Gly | |

```
CAA CTA GAC CGT GGC TGG AGA GGA AGT ACG GAT ATT ACC ATC CAA GGT          2410
Gln Leu Asp Arg Gly Trp Arg Gly Ser Thr Asp Ile Thr Ile Gln Gly
690                 695                 700                 705

GGA GAT GAC GTA TTC AAA GAG AAT TAC GTC ACA CTG CCG GGT ACC TTT          2458
Gly Asp Asp Val Phe Lys Glu Asn Tyr Val Thr Leu Pro Gly Thr Phe
                710                 715                 720

GAT GAG TGC TAT CCA ACG TAT CTA TAT CAA AAA ATA GAT GAA TCG AAA          2506
Asp Glu Cys Tyr Pro Thr Tyr Leu Tyr Gln Lys Ile Asp Glu Ser Lys
                    725                 730                 735

TTA AAA TCC TAT ACA CGT TAC GAG TTA AGA GGG TAT ATC GAG GAT AGT          2554
Leu Lys Ser Tyr Thr Arg Tyr Glu Leu Arg Gly Tyr Ile Glu Asp Ser
                740                 745                 750

CAA GAT TTA GAA ATC TAT TTG ATT CGC TAC AAT GCA AAA CAC GAA ATA          2602
Gln Asp Leu Glu Ile Tyr Leu Ile Arg Tyr Asn Ala Lys His Glu Ile
755                 760                 765

GTA AAT GTA CCA GGT ACA GGG AGT TTA TGG CCT CTT TCT ATA GAA AAT          2650
Val Asn Val Pro Gly Thr Gly Ser Leu Trp Pro Leu Ser Ile Glu Asn
770                 775                 780                 785

TCA ATT GGG CCT TGT GGA GAA CCG AAT CGC TGC GCG CCA CAC CTT GAA          2698
Ser Ile Gly Pro Cys Gly Glu Pro Asn Arg Cys Ala Pro His Leu Glu
                    790                 795                 800

TGG AAT CCT AAT CTA GAT TGT TCC TGC AGG GAC GGG GAA AAA TGT GCC          2746
Trp Asn Pro Asn Leu Asp Cys Ser Cys Arg Asp Gly Glu Lys Cys Ala
                805                 810                 815

CAT CAT TCC CAT CAT TTC TCC TTG GAC ATT GAT GTT GGA TGT ACA GAC          2794
His His Ser His His Phe Ser Leu Asp Ile Asp Val Gly Cys Thr Asp
                    820                 825                 830

TTA AAT GAG GAC TTA GGT GTA TGG GTG ATC TTC AAG ATT AAG ACG CAA          2842
Leu Asn Glu Asp Leu Gly Val Trp Val Ile Phe Lys Ile Lys Thr Gln
835                 840                 845

GAT GGC CAT GCA AGA CTA GGA AAT CTA GAG TTT CTC GAA GAG AAA CCA          2890
Asp Gly His Ala Arg Leu Gly Asn Leu Glu Phe Leu Glu Glu Lys Pro
850                 855                 860                 865

CTA TTA GGG GAA GCA CTA GCT CGT GTG AAA AGA GCG GAG AAG AAA TGG          2938
Leu Leu Gly Glu Ala Leu Ala Arg Val Lys Arg Ala Glu Lys Lys Trp
                    870                 875                 880

AGA GAC AAA CGT GAA AAA TTG GAA TGG GAA ACA AAT ATT GTT TAT AAA          2986
Arg Asp Lys Arg Glu Lys Leu Glu Trp Glu Thr Asn Ile Val Tyr Lys
                885                 890                 895

GAG GCA AAA GAA TCT GTA GAT GCT TTA TTT GTG AAC TCT CAA TAT GAT          3034
Glu Ala Lys Glu Ser Val Asp Ala Leu Phe Val Asn Ser Gln Tyr Asp
            900                 905                 910

AGA TTA CAA GCG GAT ACG AAT ATC GCG ATG ATT CAT GCG GCA GAT AAA          3082
Arg Leu Gln Ala Asp Thr Asn Ile Ala Met Ile His Ala Ala Asp Lys
915                 920                 925

CGC GTT CAT AGA ATT AGA GAA GCA TAC CTT CCA GAA TTA TCT GTA ATT          3130
Arg Val His Arg Ile Arg Glu Ala Tyr Leu Pro Glu Leu Ser Val Ile
930                 935                 940                 945

CCG GGT GTA AAT GCG GGC ATT TTC GAA GAA TTA GAG GGA CGC ATT TTC          3178
Pro Gly Val Asn Ala Gly Ile Phe Glu Glu Leu Glu Gly Arg Ile Phe
                950                 955                 960

ACA GCC TAC TCT CTA TAT GAT GCG AGA AAT GTC ATT AAA AAT GGC GAT          3226
Thr Ala Tyr Ser Leu Tyr Asp Ala Arg Asn Val Ile Lys Asn Gly Asp
                965                 970                 975

TTC AAT AAT GGT TTA TTA TGC TGG AAC TTG AAA GGG CAT GTA GAT GTA          3274
Phe Asn Asn Gly Leu Leu Cys Trp Asn Leu Lys Gly His Val Asp Val
                980                 985                 990

GAA GAA CAA AAC AAC CAT CGT TCA GTC CTT GTT GTC CCG GAA TGG GAA          3322
Glu Glu Gln Asn Asn His Arg Ser Val Leu Val Val Pro Glu Trp Glu
995                 1000                1005
```

| | | | | | | | | | | | | | | | | |
|---|---|---|---|---|---|---|---|---|---|---|---|---|---|---|---|---|
| GCA | GAG | GTG | TCC | CAA | GAA | GTT | CGT | GTC | TGT | CCA | GGT | CGT | GGC | TAT | ATC | 3370 |
| Ala | Glu | Val | Ser | Gln | Glu | Val | Arg | Val | Cys | Pro | Gly | Arg | Gly | Tyr | Ile | |
| 1010 | | | | 1015 | | | | | 1020 | | | | | 1025 | | |
| CTT | CGT | GTT | ACA | GCG | TAC | AAA | GAG | GGA | TAT | GGA | GAG | GGC | TGC | GTA | ACC | 3418 |
| Leu | Arg | Val | Thr | Ala | Tyr | Lys | Glu | Gly | Tyr | Gly | Glu | Gly | Cys | Val | Thr | |
| | | | | 1030 | | | | | 1035 | | | | | 1040 | | |
| ATT | CAT | GAG | ATC | GAA | GAC | AAT | ACA | GAC | GAA | CTG | AAA | TTT | AGC | AAC | TGT | 3466 |
| Ile | His | Glu | Ile | Glu | Asp | Asn | Thr | Asp | Glu | Leu | Lys | Phe | Ser | Asn | Cys | |
| | | | 1045 | | | | | 1050 | | | | | 1055 | | | |
| GTT | GAA | GAG | GAA | GTA | TAT | CCA | AAC | AAC | ACG | GTA | ACG | TGT | AAT | GAT | TAT | 3514 |
| Val | Glu | Glu | Glu | Val | Tyr | Pro | Asn | Asn | Thr | Val | Thr | Cys | Asn | Asp | Tyr | |
| | | 1060 | | | | | 1065 | | | | | 1070 | | | | |
| ACT | GCG | ACT | CAA | GAA | GAA | TAC | GGG | GGT | GCG | TAC | ACT | TCC | CGT | AAT | CAT | 3562 |
| Thr | Ala | Thr | Gln | Glu | Glu | Tyr | Gly | Gly | Ala | Tyr | Thr | Ser | Arg | Asn | His | |
| | 1075 | | | | | 1080 | | | | | 1085 | | | | | |
| GGA | TAT | GGC | AAA | TCT | TAT | GAA | AGT | AAT | TCT | TCC | GTA | CAA | GCT | GAT | TAT | 3610 |
| Gly | Tyr | Gly | Lys | Ser | Tyr | Glu | Ser | Asn | Ser | Ser | Val | Gln | Ala | Asp | Tyr | |
| 1090 | | | | | 1095 | | | | | 1100 | | | | | 1105 | |
| GCG | TCA | GTT | TAT | GAA | GAA | AAA | GCG | GAC | ACA | GAT | GGA | CGA | AGA | GAT | AAT | 3658 |
| Ala | Ser | Val | Tyr | Glu | Glu | Lys | Ala | Asp | Thr | Asp | Gly | Arg | Arg | Asp | Asn | |
| | | | | 1110 | | | | | 1115 | | | | | 1120 | | |
| CAT | TGC | GAA | TCT | AAC | AGA | GGG | TAT | GGG | GAT | TAC | ACG | CCA | CTA | CCA | GCT | 3706 |
| His | Cys | Glu | Ser | Asn | Arg | Gly | Tyr | Gly | Asp | Tyr | Thr | Pro | Leu | Pro | Ala | |
| | | | 1125 | | | | | 1130 | | | | | 1135 | | | |
| GGT | TAT | GTA | ACA | AAA | GAA | TTA | GAA | TAC | TTC | CCA | GAA | ACC | GAT | AAG | GTA | 3754 |
| Gly | Tyr | Val | Thr | Lys | Glu | Leu | Glu | Tyr | Phe | Pro | Glu | Thr | Asp | Lys | Val | |
| | | 1140 | | | | | 1145 | | | | | 1150 | | | | |
| TGG | GTT | GAG | ATT | GGA | GAA | ACG | GAA | GGA | ACA | TTC | ATT | GTG | GAT | AGT | GTG | 3802 |
| Trp | Val | Glu | Ile | Gly | Glu | Thr | Glu | Gly | Thr | Phe | Ile | Val | Asp | Ser | Val | |
| | 1155 | | | | | 1160 | | | | | 1165 | | | | | |
| GAA | TTA | CTC | CTT | ATG | GAG | GAA | TAAGGTATGT | | TTTAAAATGT | | AGCGTGTGCA | | | | | 3853 |
| Glu | Leu | Leu | Leu | Met | Glu | Glu | | | | | | | | | | |
| 1170 | | | | | 1175 | | | | | | | | | | | |

| | | | | | |
|---|---|---|---|---|---|
| AATAAAGAAT | GTTACTGAC | CAGTATTAAC | AGATAAATAA | GAAACTTCTA | TATAAATAAA | 3913 |
| AAACGGACAT | CAATCTTAAG | AGAATGATGT | CCGTTTTTG | TATGATTTGA | TTCAACGAGT | 3973 |
| GATATGTAAA | TATATTTTTT | TGCGAAGTCT | TTACATAACA | AAAAAATTCG | TATAGCAAAA | 4033 |
| TTCTAAATTT | AACCTTAAAT | ATAGTTAGGG | TGAAAATATG | CCAAACTAAT | TTATTCCGAA | 4093 |
| TGTTAATTCG | AAA | | | | | 4106 |

( 2 ) INFORMATION FOR SEQ ID NO:2:

( i ) SEQUENCE CHARACTERISTICS:
        ( A ) LENGTH: 1176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Asn | Asn | Ile | Gln | Asn | Gln | Cys | Val | Pro | Tyr | Asn | Cys | Leu | Ser |
| 1 | | | | 5 | | | | 10 | | | | | 15 | | |
| Asn | Pro | Glu | Glu | Ile | Leu | Leu | Asp | Gly | Glu | Arg | Ile | Ser | Thr | Gly | Asn |
| | | 20 | | | | | 25 | | | | | 30 | | | |
| Ser | Ser | Ile | Asp | Ile | Ser | Leu | Ser | Leu | Val | Gln | Leu | Leu | Val | Ser | Asn |
| | | 35 | | | | 40 | | | | | 45 | | | | |
| Phe | Val | Pro | Gly | Gly | Gly | Phe | Leu | Val | Gly | Leu | Leu | Asp | Phe | Val | Trp |
| | 50 | | | | | 55 | | | | | 60 | | | | |
| Gly | Ile | Val | Gly | Pro | Ser | Pro | Trp | Asp | Ala | Phe | Leu | Val | Gln | Ile | Glu |

-continued

| | 65 | | | | 70 | | | | 75 | | | | 80 | |
|---|---|---|---|---|---|---|---|---|---|---|---|---|---|---|
| Gln | Leu | Ile | Asn | Glu | Arg | Ile | Ala | Ala | Tyr | Ala | Arg | Ser | Ala | Ala | Ile |
| | | | | 85 | | | | 90 | | | | | 95 | | |
| Ser | Asn | Leu | Glu | Gly | Leu | Gly | Asn | Asn | Phe | Asn | Ile | Tyr | Val | Glu | Ala |
| | | | 100 | | | | 105 | | | | | 110 | | | |
| Phe | Lys | Glu | Trp | Glu | Ala | Asp | Pro | Asp | Asn | Pro | Val | Thr | Arg | Thr | Arg |
| | | 115 | | | | 120 | | | | | 125 | | | | |
| Val | Val | Asp | Arg | Phe | Arg | Ile | Leu | Asp | Gly | Leu | Leu | Glu | Arg | Asp | Ile |
| | 130 | | | | 135 | | | | | 140 | | | | | |
| Pro | Ser | Phe | Arg | Ile | Ala | Gly | Phe | Glu | Val | Pro | Leu | Leu | Ser | Val | Tyr |
| 145 | | | | | 150 | | | | | 155 | | | | | 160 |
| Ala | Gln | Ala | Ala | Asn | Leu | His | Leu | Ala | Ile | Leu | Arg | Asp | Ser | Ser | Ile |
| | | | | 165 | | | | 170 | | | | | 175 | | |
| Phe | Gly | Ala | Arg | Trp | Gly | Leu | Thr | Thr | Ile | Asn | Val | Asn | Glu | Asn | Tyr |
| | | | 180 | | | | 185 | | | | | 190 | | | |
| Asn | Arg | Leu | Ile | Arg | His | Ile | Asp | Glu | Tyr | Ala | Asn | His | Cys | Ala | Asp |
| | | 195 | | | | 200 | | | | | 205 | | | | |
| Thr | Tyr | Asn | Arg | Gly | Leu | Asn | Asn | Leu | Pro | Lys | Ser | Thr | Tyr | Gln | Asp |
| | 210 | | | | 215 | | | | | 220 | | | | | |
| Trp | Ile | Thr | Tyr | Asn | Arg | Leu | Arg | Arg | Asp | Leu | Thr | Leu | Thr | Val | Leu |
| 225 | | | | | 230 | | | | 235 | | | | | | 240 |
| Asp | Ile | Ala | Ala | Phe | Phe | Pro | Ser | Tyr | Asp | Asn | Arg | Arg | Tyr | Pro | Ile |
| | | | | 245 | | | | 250 | | | | | 255 | | |
| Gln | Ser | Val | Gly | Gln | Leu | Thr | Arg | Glu | Ile | Tyr | Thr | Asp | Pro | Leu | Ile |
| | | | 260 | | | | 265 | | | | | 270 | | | |
| Thr | Phe | Asn | Pro | Gln | Leu | Gln | Ser | Val | Ala | Gln | Leu | Pro | Thr | Phe | Asn |
| | | 275 | | | | 280 | | | | | 285 | | | | |
| Val | Met | Glu | Ser | Asn | Ala | Ile | Arg | Thr | Pro | His | Leu | Phe | Asp | Val | Leu |
| | 290 | | | | 295 | | | | | 300 | | | | | |
| Asn | Asn | Leu | Thr | Ile | Phe | Thr | Asp | Trp | Phe | Ser | Val | Gly | Arg | Asn | Phe |
| 305 | | | | 310 | | | | 315 | | | | | | | 320 |
| Tyr | Trp | Gly | Gly | His | Arg | Val | Ile | Ser | Asn | Arg | Ile | Gly | Gly | Gly | Asn |
| | | | | 325 | | | | 330 | | | | | 335 | | |
| Ile | Thr | Ser | Pro | Ile | Tyr | Gly | Arg | Glu | Ala | Asn | Gln | Glu | Pro | Pro | Arg |
| | | | 340 | | | | 345 | | | | | 350 | | | |
| Ser | Phe | Thr | Phe | Asn | Gly | Pro | Val | Phe | Arg | Thr | Leu | Ser | Asn | Pro | Thr |
| | | 355 | | | | 360 | | | | | 365 | | | | |
| Phe | Arg | Pro | Leu | Gln | Gln | Pro | Trp | Pro | Ala | Pro | Pro | Phe | Asn | Leu | Arg |
| | 370 | | | | 375 | | | | | 380 | | | | | |
| Gly | Val | Glu | Gly | Val | Glu | Phe | Ser | Thr | Pro | Leu | Asn | Ser | Phe | Thr | Tyr |
| 385 | | | | | 390 | | | | | 395 | | | | | 400 |
| Arg | Gly | Arg | Gly | Thr | Val | Asp | Ser | Leu | Thr | Glu | Leu | Pro | Pro | Glu | Asp |
| | | | | 405 | | | | | 410 | | | | | 415 | |
| Asn | Ser | Val | Pro | Pro | Arg | Glu | Gly | Tyr | Ser | His | Arg | Leu | Cys | His | Ala |
| | | | 420 | | | | | 425 | | | | | 430 | | |
| Thr | Phe | Val | Gln | Arg | Ser | Gly | Thr | Pro | Phe | Leu | Thr | Thr | Gly | Pro | Val |
| | | | 435 | | | | 440 | | | | | 445 | | | |
| Phe | Ser | Trp | Thr | His | Arg | Ser | Ala | Thr | Asp | Arg | Asn | Ile | Ile | Tyr | Pro |
| | | 450 | | | | 455 | | | | | 460 | | | | |
| Asp | Val | Ile | Asn | Gln | Ile | Pro | Leu | Val | Lys | Ala | Phe | Asn | Leu | Thr | Ser |
| 465 | | | | | 470 | | | | | 475 | | | | | 480 |
| Gly | Thr | Ser | Val | Val | Arg | Gly | Pro | Gly | Phe | Thr | Gly | Gly | Asp | Ile | Ile |
| | | | | 485 | | | | | 490 | | | | | | 495 |

```
Arg Thr Asn Val Asn Gly Ser Val Leu Ser Met Ser Leu Asn Phe Ser
            500                 505                 510

Asn Thr Thr Leu Gln Arg Tyr Arg Val Arg Val Arg Tyr Ala Ala Ser
            515                 520                 525

Gln Thr Met Val Met Ser Val Thr Val Gly Gly Ser Thr Thr Gly Asn
            530                 535                 540

Gln Gly Phe Pro Ser Thr Met Ser Ala Asn Gly Ala Leu Thr Ser Gln
545                 550                 555                 560

Ser Phe Arg Phe Ala Glu Phe Pro Val Gly Ile Ser Ala Ser Gly Ser
                565                 570                 575

Gln Gly Ala Ser Ile Ser Ile Ser Asn Asn Val Gly Arg Gln Met Phe
            580                 585                 590

His Leu Asp Arg Ile Glu Phe Leu Pro Val Thr Ser Thr Phe Glu Glu
            595                 600                 605

Glu Tyr Asp Leu Glu Arg Ala Gln Glu Ala Val Asn Ala Leu Phe Thr
    610                 615                 620

Ser Thr Asn Gln Leu Gly Leu Lys Thr Asp Val Thr Asp Tyr His Ile
625                 630                 635                 640

Asp Gln Val Ser Asn Leu Val Glu Cys Leu Ser Asp Glu Phe Cys Leu
                645                 650                 655

Asp Glu Lys Arg Glu Leu Ser Glu Lys Val Lys His Ala Lys Arg Leu
            660                 665                 670

Ser Asp Glu Arg Asn Leu Leu Gln Asp Arg Asn Phe Arg Ser Ile Asn
    675                 680                 685

Gly Gln Leu Asp Arg Gly Trp Arg Gly Ser Thr Asp Ile Thr Ile Gln
    690                 695                 700

Gly Gly Asp Asp Val Phe Lys Glu Asn Tyr Val Thr Leu Pro Gly Thr
705                 710                 715                 720

Phe Asp Glu Cys Tyr Pro Thr Tyr Leu Tyr Gln Lys Ile Asp Glu Ser
                725                 730                 735

Lys Leu Lys Ser Tyr Thr Arg Tyr Glu Leu Arg Gly Tyr Ile Glu Asp
            740                 745                 750

Ser Gln Asp Leu Glu Ile Tyr Leu Ile Arg Tyr Asn Ala Lys His Glu
    755                 760                 765

Ile Val Asn Val Pro Gly Thr Gly Ser Leu Trp Pro Leu Ser Ile Glu
770                 775                 780

Asn Ser Ile Gly Pro Cys Gly Glu Pro Asn Arg Cys Ala Pro His Leu
785                 790                 795                 800

Glu Trp Asn Pro Asn Leu Asp Cys Ser Cys Arg Asp Gly Glu Lys Cys
                805                 810                 815

Ala His His Ser His His Phe Ser Leu Asp Ile Asp Val Gly Cys Thr
            820                 825                 830

Asp Leu Asn Glu Asp Leu Gly Val Trp Val Ile Phe Lys Ile Lys Thr
    835                 840                 845

Gln Asp Gly His Ala Arg Leu Gly Asn Leu Glu Phe Leu Glu Glu Lys
    850                 855                 860

Pro Leu Leu Gly Glu Ala Leu Ala Arg Val Lys Arg Ala Glu Lys Lys
865                 870                 875                 880

Trp Arg Asp Lys Arg Glu Lys Leu Glu Trp Glu Thr Asn Ile Val Tyr
            885                 890                 895

Lys Glu Ala Lys Glu Ser Val Asp Ala Leu Phe Val Asn Ser Gln Tyr
            900                 905                 910

Asp Arg Leu Gln Ala Asp Thr Asn Ile Ala Met Ile His Ala Ala Asp
    915                 920                 925
```

```
Lys  Arg  Val  His  Arg  Ile  Arg  Glu  Ala  Tyr  Leu  Pro  Glu  Leu  Ser  Val
     930                 935                      940

Ile  Pro  Gly  Val  Asn  Ala  Gly  Ile  Phe  Glu  Glu  Leu  Glu  Gly  Arg  Ile
945                      950                 955                           960

Phe  Thr  Ala  Tyr  Ser  Leu  Tyr  Asp  Ala  Arg  Asn  Val  Ile  Lys  Asn  Gly
                    965                      970                      975

Asp  Phe  Asn  Asn  Gly  Leu  Leu  Cys  Trp  Asn  Leu  Lys  Gly  His  Val  Asp
               980                      985                           990

Val  Glu  Glu  Gln  Asn  Asn  His  Arg  Ser  Val  Leu  Val  Val  Pro  Glu  Trp
          995                           1000                     1005

Glu  Ala  Glu  Val  Ser  Gln  Glu  Val  Arg  Val  Cys  Pro  Gly  Arg  Gly  Tyr
          1010                 1015                     1020

Ile  Leu  Arg  Val  Thr  Ala  Tyr  Lys  Glu  Gly  Tyr  Gly  Glu  Gly  Cys  Val
1025                     1030                 1035                          1040

Thr  Ile  His  Glu  Ile  Glu  Asp  Asn  Thr  Asp  Glu  Leu  Lys  Phe  Ser  Asn
                    1045                     1050                     1055

Cys  Val  Glu  Glu  Glu  Val  Tyr  Pro  Asn  Asn  Thr  Val  Thr  Cys  Asn  Asp
               1060                      1065                     1070

Tyr  Thr  Ala  Thr  Gln  Glu  Glu  Tyr  Gly  Gly  Ala  Tyr  Thr  Ser  Arg  Asn
               1075                      1080                     1085

His  Gly  Tyr  Gly  Lys  Ser  Tyr  Glu  Ser  Asn  Ser  Ser  Val  Gln  Ala  Asp
     1090                      1095                     1100

Tyr  Ala  Ser  Val  Tyr  Glu  Glu  Lys  Ala  Asp  Thr  Asp  Gly  Arg  Arg  Asp
1105                     1110                 1115                          1120

Asn  His  Cys  Glu  Ser  Asn  Arg  Gly  Tyr  Gly  Asp  Tyr  Thr  Pro  Leu  Pro
                    1125                     1130                     1135

Ala  Gly  Tyr  Val  Thr  Lys  Glu  Leu  Glu  Tyr  Phe  Pro  Glu  Thr  Asp  Lys
               1140                      1145                     1150

Val  Trp  Val  Glu  Ile  Gly  Glu  Thr  Glu  Gly  Thr  Phe  Ile  Val  Asp  Ser
          1155                      1160                     1165

Val  Glu  Leu  Leu  Leu  Met  Glu  Glu
     1170                     1175
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CTATCAGAAT TCTGGTAGTT TAAT                                             24
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CGGAGGTATT CCATGGAGGA AAATAATC                                         28
```

( 2 ) INFORMATION FOR SEQ ID NO:5:

( i ) SEQUENCE CHARACTERISTICS:
        ( A ) LENGTH: 29 base pairs ( B ) TYPE: nucleic acid
        ( C ) STRANDEDNESS: single
        ( D ) TOPOLOGY: linear ( x i ) SEQUENCE DESCRIPTION: SEQ ID NO:5:

CCACAGTTAC AGTCTGTAGC TCAATTACC                                              29

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGTAATTGAG CTACAGACTC TAACTGTGG                                              29

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CGCTACTAAT AGAACCTGCA CCA                                                    23

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGTCGTGGCT ATATCCTTCG TGTCACAG                                               28

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCACGCTATC CACGATGAAT GTTCCTTC                                               28

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTATCTGTCG ACTATAGGTC AGTAA                                                  25

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single

```
        ( D ) TOPOLOGY: linear ( x i ) SEQUENCE DESCRIPTION: SEQ ID NO:11:

GGAGAAAGAT GGGGATTGAC                                                          20

( 2 ) INFORMATION FOR SEQ ID NO:12:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:12:

GTCATAGCTG TTTCCTG                                                             17

( 2 ) INFORMATION FOR SEQ ID NO:13:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:13:

CAGGAAACAG CTATGAC                                                             17
```

METHOD OF CONTROLLING INSECT WITH NOVEL INSECTICIDAL PROTEIN

This is a Divisional of application Ser. No. 08/197,998, filed on Feb. 16, 1994, now abandoned which is a Continuation of application Ser. No. 08/102,316, filed on Aug. 5, 1993, now abandoned, which is a Continuation of application Ser. No. 08/004,474, filed Jan. 14, 1993, now abandoned, which is a Continuation of application Ser. No. 07/844,302, filed Feb. 27, 1992, now abandoned.

This invention relates to a novel protein with insecticidal properties, nucleic acid sequences encoding this protein, and use of this protein to control insects.

BACKGROUND OF THE INVENTION

Many bacteria belonging to the species *Bacillus thuringiensis* (*B.t.*) produce crystal protein toxins which have insecticidal properties. The most studied crystal protein genes to date have been those which are active against Lepidoptera. One group of toxins, designated CryIC, has also been shown to be toxic to Spodoptera as well.

Two Spodoptera-active cryIC genes from *B.t. aizawai* and *B.t. entomocidus* have been reported by Sanchis et al, 1989, *Mol. Microbiol.* 3:229–238 and Honee et al, 1988, *Nucl. Acids Res.* 16:6240, both of which are hereby incorporated by reference. These two genes were found to code for toxins that differ by a small number of amino acid substitutions. Bosse et al, 1990, *Nucl. Acids Res.* 18:7443 describe a gene from *B.t. kenyae* which they identify as a cryIC(b), whose protein is toxic to *Bombyx mori*.

It would be desirable to identify other genes which encode toxins active against Spodoptera.

DESCRIPTION OF THE INVENTION

This invention relates to novel proteins which exhibit insecticidal activity against Lepidoptera, including Spodoptera, their nucleic acid sequences, and use of these proteins to control various insects.

In accordance with this invention, it has been found that *B.t. galleriae* strain HD29 contains DNA sequences which hybridize to the cryIC gene from *B.t. aizawai* strain HD229, yet are not significantly homologous. These new sequences have been isolated and characterized and are designated cryIC(b).

As used throughout the specification and claims, the following definitions apply:

Isolated polypeptide—a polypeptide which is no longer associated with *B.t. galleriae*, or the cell which naturally produces it.

Substantially homologous—an amino acid sequence is substantially homologous to the full length CryIC(b) sequence if it is at least 90% homologous to CryIC(b) in the so-called "heterologous region" which occurs between amino acid 451–650, inclusive, and shows substantially the same bioactivity as CryIC(b).

Stringent hybridization conditions—those in which hybridization is effected in a standard manner at 65° C. in 4× buffered saline (a.k.a. SSPE buffer) followed by washing at 52° C. in 0.2× SSPE, which will not affect true hybrids which have formed.

Substantial bioactivity—a truncated toxin or full length polypeptide possesses substantially the same bioactivity as CryIC(b) if, in assays against Lepidopteran insects, including Spodoptera, activity is not statistically significantly different.

Truncated toxin—the portion of a protein which, after ingestion and cleavage by an insect, exhibits insecticidal activity.

Figure 1:
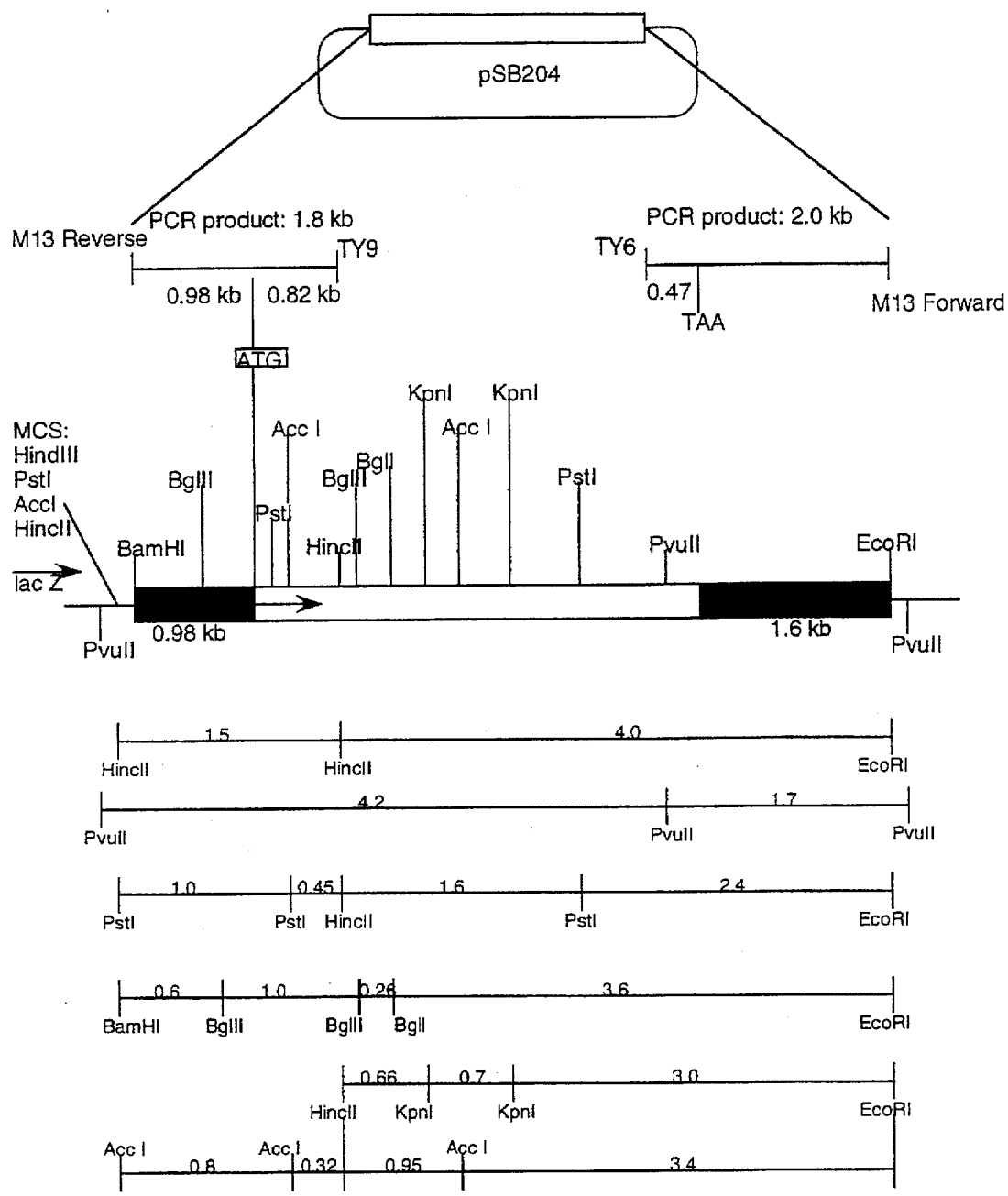
FIG. 1 is a diagram of pSB204 and the restriction sites found. Section A illustrates the result of PCR analysis which orients the cryIC(b) gene within the plasmid pSB204. The combination of M13 Reverse and TY9 primers gave a 1.8 kb product, indicating the first amino acid residue of the protein is −0.98 kb from the BamHI site in the polylinker. The combination of M13 Universal and TY6 primers gave a 2 kb product, indicating the stop codon is −1.6 kb from the EcoRI site in the polylinker. Section B is a summary of the restriction digests performed.
Figure 2:
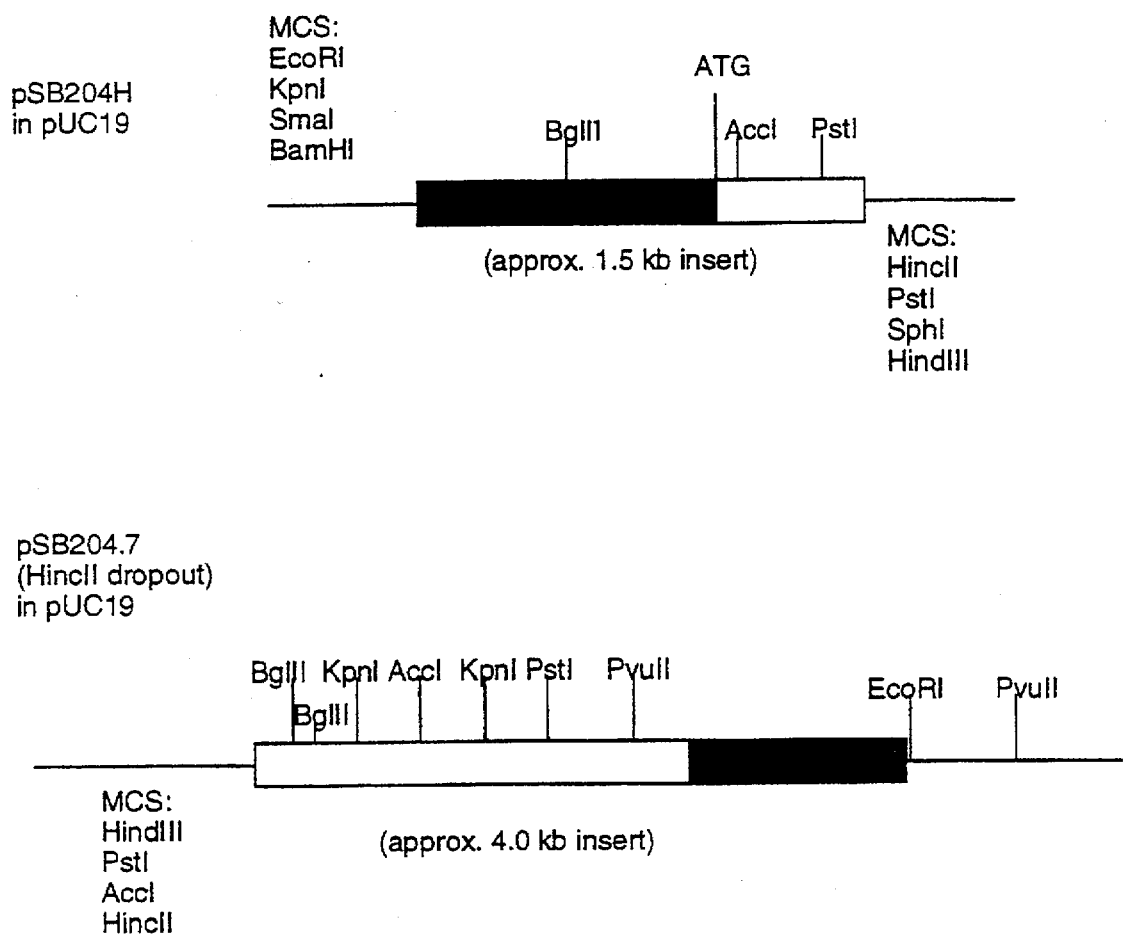
FIG. 2 illustrates two subclones used for DNA sequencing. pSB204H has a 1.5 kb HincII-BamHI fragment ligated into pUC19. pSB204.7 has the 1.5 kb HincII-BamHI piece removed, made by religating pSB204 to itself at the HincII site.

The complete sequence of the novel protein is given in TABLE 1, below (SEQ. ID. NO.: 1 and SEQ. ID. NO.: 2). The CryIC(b) protein is 1176 amino acids long with a predicted molecular weight of 133 kDa1. Thus one aspect of this invention comprises an isolated polypeptide having insecticidal activity characterized by having the amino acid sequence given in TABLE 1, or a polypeptide with substantial homology thereto.

It is known in the art that proteins produced by *Bacillus thuringiensis* varieties occur as a protoxin. As the insect ingests this toxin, it is cleaved, and the activated or truncated toxin then exhibits insecticidal activity. The full length sequence discussed above is thus the protoxin form of the polypeptide. This invention also includes the truncated toxin form of the polypeptide as well.

The naturally occurring DNA sequence of the full length polypeptide has also been determined, as is given in TABLE 1. As is known in the art the degeneracy of the genetic code allows for various nucleic acid sequences (DNAs and RNAs) to encode the same protein. When cloning this gene in another host organism, it may prove desirable to alter the DNA codons such that those preferred by the host organism are employed, although no changes are made in the translation product. Thus, all these DNAs comprise another aspect of this invention. Further, it may be desirable to clone only the truncated toxin. Thus this invention also includes nucleic acid sequences (DNAs and RNAs) which encode the truncated toxin, using either the naturally occurring codons, or other codons expressing the same amino acids. Additionally, it is recognized that minor changes in the nucleic acid sequences may result in minor changes which result in the production of a "substantially homologous" polypeptide. Thus this invention also is directed to nucleic acids which will hybridize under stringent conditions to the naturally occurring sequence.

Vectors comprising the cryIC(b) gene are yet another part of this invention. The vectors are generally a known vector, and are chosen for their suitability for use with the desired host cell. Those of ordinary skill in the art will be able to determine appropriate vectors. A gene construct is made, comprising a promoter which is expressed in the host cell, operably linked to the cryIC(b) gene of this invention; optionally other 3' or 5' elements which enhance expression, and known to those of ordinary skill in the art, may also be included in the construct.

A further aspect of this invention is a cell which is transformed with a vector comprising a gene encoding a polypeptide of this invention. The cell may be another prokaryotic cell, such as E. coli or other Bacillus species. Alternatively, a B.t. galleriae may be transformed with additional copies of the cryIC(b) gene to boost production of the CryIC(b) protein. Also considered as part of this invention are eukaryotic cells, especially plant cells, so that the transformed plants have insecticidal properties. Also included is a virus, such as a baculovirus which has been transformed with the cryIC(b) gene so that its native insecticidal activity is enhanced.

CryIC(b) was compared at the DNA and amino acid levels to the following published sequences of other cryI-type genes and proteins:

cryIA(a) Schnepf, et al 1985. *J. Biol. Chem.* 260:6264.
cryIA(b) Hofte et al. 1986. *Eur. J. Biochem.* 161:273.
cryIA(c) Adang et al. 1985 *Gene* 36:289.
cryIC Honee, et al. 1988. *Nucl. Acids Res.* 16:6240.
cryIC(b) Bosse et al. 1990. *Nucl. Acids Res.* 18:7443.
cryIE Visser et al. 1990 *J. Bact.* 172:6783–88.

When compared to the DNA sequence of cryIC from *B.t. entomocidus*, it was found that the differences between the two are limited primarily to a heterologous region between nucleotides 1646 and 2190. The overall identity between the two sequences is 87%. Comparisons were made at the amino acid level with other cryI-type protein translations in two ways: by looking at entire amino acid translations, or by dividing the translations into three regions: 1) the first 450 amino acids; 2) amino acids 451–650, which corresponds to the heterologous region; and 3) amino acids 651 to the end of the translation. These results are given in TABLE 2, below. In this table, the numbers given are the % similarity/% identity.

TABLE 2

| | Translation Comparisons | | | |
|---|---|---|---|---|
| CryIC(b) vs: | 1–450* | 451–650* | 651–end* | Overall** |
| CryIC | 95/92 | 68/53 | 96/93 | 90/86 |
| CryIC(b) | 63/46 | 68/52 | 96/93 | 78/69 |
| CryIA(a) | 69/51 | 64/53 | 95/92 | 80/70 |
| CryIA(b) | 68/50 | 64/52 | 96/93 | 63/45 |
| CryIA(c) | 68/50 | 65/50 | 94/91 | 79/68 |
| CryIE | 65/49 | 68/53 | 95/93 | 79/70 |

*Bestfit (GCG, Univ. Wisconsin) computer program comparison
**Gap/Limit (GCG, Univ. Wisconsin) computer program comparison As can be seen, there is a great similarity to the CryIC protein in the first and third segments (95% and 96%), but the region between amino acids 450 and 650 only had 68% homology. When the intact translations are compared, the two showed 90% similarity at the amino acid level. When compared to the other CryI-type protein translations, there is a consistently high degree of homology with the third segment which contains the carboxy-terminal portion of the crystal protein, but none of the other comparisons, either between segments or between intact translations showed the same degree of similarity as seen with the CryIC comparisons.

The CryIC(b) protein of this invention shows toxicity towards various insects, including those of the order Lepidoptera, including Spodoptera. Thus one aspect of this invention comprises an insecticidal composition comprising as its active ingredient an insecticidal amount of a CryIC(b) protein. The CryIC(b) protein producing organism or the CryIC(b) protein may be formulated in a number of ways. For example, they may in the form of wettable powder, granules, or dusts. They may be mixed with various known inert materials including inorganic minerals or organic matter (such as hulls, corncobs, and the like). Additionally included in the formulations may be spreader-sticker adjuvants, stabilizing agents, other pesticidal additives, or equivalents. Liquid formulations may be either aqueous-based or non-aqueous based and may be foams, gels, suspensions, emulsifiable concentrates, or the like. Other ingredients including surfactants or dispersants may also be included.

The amount of active ingredient will vary depending on many factors, including the nature of the particular formulation. For dry formulations the inactive ingredient will be present in at least 1% to 95% by weight, while in liquid formulation, this amount may be somewhat reduced. The application rate will vary depending on a number of factors, including the pest to be controlled and the climate conditions, but will generally be in the range of 0.5 to 100 kg/hectare, preferably 10–50 kg/hectare.

The following non-limiting Examples are presented to better illustrate this invention.

EXAMPLE 1

Library Construction

Approximately 2 µg of *B.t. galleriae* genomic DNA is restricted with EcoRI and separated by electrophoresis on a 0.6% agarose gel. A slice containing fragments of approximately 9–11 kb is cut from the gel and electroeluted into 0.75 inch dialysis tubing in 0.5% TBE (Maniatis et al. 1982, *Molecular Cloning: A Laboratory Manual* Cold Spring Harbor Press). The eluate is purified using an Elutip-d column followed by ethanol precipitation and the resulting dried pellet is resuspended in 15 µl water to a concentration of 0.12 µg/µl.

0.2 µg of the purified 9–11 kb sized fraction is ligated to 1.0 µg of λDashII EcoRI arms (Stratagene) in a 5 µl volume under conditions recommended by the manufacturer. 1.5 µl of the ligation mixture is packaged into phage particles using the high efficiency GigaPack Gold packaging extract (Stratagene). The titre of the resulting subgenomic library is $3.1 \times 10^6$ plaque forming units per µg DNA.

Polymerase Chain Reaction (PCR)

The oligonucleotide primers used in this study are listed in TABLE 3, below. (SEQ. ID. NOS. 3 to 10). For PCR analysis of the λ phages, 4 µl of a 100 µl phage stock is used for template DNA. Concentration of the genomic DNA in the PCR reactions is between 0.1 and 0.5 µg and the concentrations of other components are as recommended in the Perkin Elmer Cetus GeneAmp Kit. The PCR conditions used for probe generation are 25 cycles of 94° C. for 1 min, 52° C. for 2 min, and 72° C. for 3 min followed by a 7 min incubation at 72° C.

TABLE 3

OLIGONUCLEOTIDE PRIMERS

| Name | Sequence | Nt[1] | Strand[2] | Site[3] | SEQ. ID. NO. |
|------|----------|-------|-----------|---------|--------------|
| PCR1 | CTATCAGAATTCTGGTAGTTTAAT | 3–26 | c | EcoRI | SEQ. ID. NO.: 3 |
| TY8 | CGGAGGTATTCCATGGAGGAAAATAATC | 34–61 | c | NcoI | SEQ. ID. NO.: 4 |
| galP1 | CCACAGTTACAGTCTGTAGCTCAATTACC | 871–899 | c | | SEQ. ID. NO.: 5 |
| TY9 | GGTAATTGAGCTACAGACTCTAACTGTGG | 871–899 | nc | | SEQ. ID. NO.: 6 |
| galP2 | CCGCTACTAATAGAACCTGCACCA | 1831–1854 | nc | | SEQ. ID. NO.: 7 |
| TY6 | GGTCGTGGCTATATCCTTCGTGTCACAG | 3146–3173 | c | | SEQ. ID. NO.: 8 |
| TY7 | CCACGCTATCCACGATGAATGTTCCTTC | 3566–3592 | nc | | SEQ. ID. NO.: 9 |
| PCR4 | TTATCTGTCGACTATAGGTCAGTAA | 3656–3179 | nc | SalI | SEQ. ID. NO.: 10 |

[1]The nucleotide (nt.) numbers are based on the sequence of the B.t. entomocidus cryIC gene in Honee et al, 1988, supra.
[2]"c" indicates that the primer matches the sequence of the coding strand and hybridizes to the noncoding strand. "nc" means that the primer sequence matches the noncoding strand.
[3]The sites listed are designed into the oligonucleotide primers to facilitate cloning by introducing nucleotide mismatches.

To generate a hybridization probe, PCR is performed using B.t. aizawai HD229 DNA as a template and primers galP1 and galP2 (SEQ. ID. NO.: 5 and SEQ. ID. NO.: 7). These two primers are designed to hybridize to regions of the B.t. entomocidus cryIC gene that are not present in the HD1 cryIA(a) gene, and the primers spanned the region which shared the least homology with the cryIA(a) gene. The resulting PCR-generated probe is a 984 bp fragment from the variable region of the B.t. aizawai cryIC gene.

Hybridization Screening

Plaque lifts are done on the Bio-Rad Plaque Lift Membranes according to the manufacturer's instructions. Plaque lift hybridizations are performed using the same conditions as described below for Southern Blotting.

Southern Blotting

Total DNA from B.t. aizawai strain HD229 and B.t. galleriae strain HD29 are restricted with EcoRI. A HindIII and an EcoRI digest are also performed on B.t. galleriae TY10 (which is isogeneic to strain HD29) to confirm the results. These four digests are then subjected to electrophoresis on a 0.6% agarose gel and the DNA is transferred for the gel to Zeta Probe nylon membrane using a vacuum blot apparatus. Under low stringency conditions (45° C.), the probe hybridized strongly to an 8 kb EcoRI fragment from B.t. aizawai HD229 and more weakly to an approximately 10 kb EcoRI fragment from B.t. galleriae strains HD29 and TY10. The probe also hybridizes to an approximately 14 kb HindIII fragment from strain TY10.

Phage Isolation and Characterization

A subgenomic library is constructed in the λDashII vector (described supra) to isolate the B.t. galleriae 10 kb EcoRI fragment containing sequences which hybridize to the B.t. aizawai cryIC gene. Of 7800 phages that are screened, 45 are positive. Twelve of these positive are plaque purified, and the are found to fall into two classes, based on the strength of the hybridization signals. Three phages, (#7, #9, and #34) hybridize weakly and nine hybridize strongly. One of the strongly-hybridizing phages, #42, is chosen for further study.

A Southern blot is performed to identify the fragments which contain coding sequences and/or the intact gene. A 5.5 kb BamHI-EcoRI fragment is identified and subcloned in the E. coli vector pUC19, and this construct is referred to as pSB204.

EXAMPLE 2

Phage DNA Isolation

Phage DNA is isolated using Qiagen Lambda DNA columns, according to manufacturer's instructions. The phage are PEG-precipitated from a 100 ml overnight culture, treated with the buffers provided in the Qiagen Lambda kit, and purified using the Qiagen pack-500 column.

Southern Transfer

Probe Preparation

Products form PCR are gel-purified and then radiolabelled using the Random Primers Kit from BRL under the recommended conditions. The labelled probe is separated from unincorporated label using a BioSpin columns from BioRad.

Blotting

Approximately 1 μg of phage DNA is restricted with BamHI and EcoRI enzymes under high salt conditions and is electrophoresed on an 0.8% agarose/1×TBE gel. After depurinating the DNA by soaking the gel in 0.25M HCl for 10 minutes, the gel is transferred to a solution of 0.4M NaOH and vacuum blotted onto a ZetaProbe membrane (BioRad) for 30 minutes. The membrane is dried under a vacuum for 30 minutes at 80° C.

Hybridization Conditions

The dried ZetaProbe membrane is prehybridized in 15 ml of 1 mM EDTA, 0.5M NaH$_2$PO$_4$ (pH 7.2), and 7% SDS for five minutes at 65° C. The prehybridization solution is replaced with the same solution, to which is added the denatured, labelled probe. The blot with the N-terminal probe is incubated overnight at 45° C. and the blot with the C-terminal probe is incubated at 65° C. overnight. The next day both blots are washed using the recommended conditions for ZetaProbe, except that the N-terminal blot is washed at 45° C. After air-drying, both blots are used to expose XAR film.

Polymerase Chain Reaction

In addition to primers TY6, TY7, TY8, TY9, galP1 and galP2, given in Table 3, supra, three other PCR primers are made:

229C GGAGAAAGATGGGGATTGAC (SEQ. ID. NO.: 11)

M13 Forward GTCATAGCTGTTTCCTG (SEQ. ID. NO.: 12)

M13 Reverse CAGGAAACAGCTATGAC (SEQ. ID. NO.: 13)

Samples of DNA are amplified by 25 cycles of denaturing at 94° C. for one minute, annealing at 52° C. for two minutes and extending at 72° C. for three minutes.

PCR is used to demonstrate that the construct with the 5.5 kb insert carries an intact gene. The primers used were 229C, a primer based on the *B.t. entomocidus* cryIC sequence which hybridizes to the non-coding strand at 531 bp downstream of the start codon of cryIC, and TY7, which hybridizes to the coding strand at 23 bases upstream from the stop codon of the *B.t. entomocidus* sequence. The subclone of the 5.5 kb fragment is positive and generates a product of approximately 3 kb in length, which indicates that this subclone would carry an intact gene. A second set of PCRs is performed to orient the insert within the plasmid, now named pSB204. The combination of M13 Reverse and TY9 primers gives a 1.8 kb product, which indicates that the first amino acid residue of the protein is approximately 0.98 kb from the BamHI site in the polylinker of the vector. The combination of M13 Universal with TY6 primers gives a 2 kb product, indicating that the stop codon is approximately 1.6 kb from the EcoRI site in the polylinker.

A summary of the restriction digests performed is given in FIG. 1 and a list of fragment sizes generated by the restriction enzymes is given in TABLE 4, below.

TABLE 4

| Restriction Enzyme | Fragment sizes (kb) |
|---|---|
| PstI | 5.4, 2.1, 1.0 |
| KpnI | 7.6, 0.7 |
| SmaI | uncut |
| PvuII | 4.2, 2.4, 1.7 |
| BglII | 6.9, 1.1, 0.15 |
| HincII | 7.0, 1.45 |
| AccI | 6.1, 1.4, 0.8, 0.22 |
| BamHI + BglII | 6.3, 1.1, 0.6, 0.25 |
| BglII + HincII | 6.3, 0.8, 0.65 (2) |
| AccI + HincII | 6.1, 0.95, 0.85, 0.22 |
| KpnI + EcoRI | 4.7, 3.0, 0.7 |
| PstI + HincII | 5.4, 1.6, 0.95, 0.5 |
| PvuII + HincII | 2.4, 2.3, 1.7, 1.5, 0.6, 0.3 |

The restriction pattern of this new gene is compared to that of other cryIC genes, including *B.t. entomocidus* 60.5. Some similarities as well as some differences are noted. In both genes, there is an AccI site approximately 200 bp from the start codon. However, the *B.t. galleriae* gene is missing an AccI site found in the 3' regions of the other two cryIC genes. A PvuII site is found in the C-terminus of both these cryIC genes as well as in the 3' regions of cryIA(a), cryIA(b) and cryIC(c). Both the *B.t. galleriae* and *B.t. entomocidus* genes appear to contain a BglII site approximately 1 kb from the start codon. The *B.t. galleriae* gene contains an additional BglII site approximately 200 bp upstream of this site.

A unique HincII site is identified in the gene of this invention. The PCR data indicate that this site is approximately 550 bp downstream of the start codon. Based on this, two further subclones are created for DNA sequencing. The first, pSB240H contains a 1.5 kb HincII-BamHI fragment ligated into pUC19. The second, pSB204.7 eliminates the ~5 kb HincII-BamHI fragment by religating the pSB204 plasmid to itself at the HincII site (See FIG. 2).

SDS-PAGE and Western Transfer

Samples for each are prepared as follows. One ml of a two ml culture that is grown in LB for two days at 37° C. is pelleted and resuspended in 0.1 ml $H_2O$. Twenty-five µl of this is mixed with 25 µl of 2× Loading Buffer (4 ml 10% SDS, 1 ml Tris-HCl, 4 ml 50% glycerol, 0.4 ml methanol, 0.5 ml $H_2O$, 0.1 ml Bromophenol blue), and boiled for three minutes. 5 µl of this is loaded onto an 8% polyacrylamide gel. The gel is electrophoresed and then stained with Coomassie Blue. For a Western transfer, the gel is not stained, but is electroblotted onto nitrocellulose, using a standard protocol set forth below. It is then reacted with antisera that is raised using standard procedures against the purified crystals from strain SA11 or HD229.

A Southern blot is performed to locate the amino and carboxy terminal coding regions of the toxin gene within the phage. The amino terminal probe is made by PCR from 100 ng of HD229 DNA using the primers TY8 and galP2 and is approximately 1 kb in length. The carboxy terminal probe is made from 100 ng HD29 DNA using the primers TY6 and TY7 and is approximately 0.45 kb in length. Bands at 4.5 and 5.5 kb from a BamHI-EcoRI digest hybridize to both probes. These fragments are gel-purified and ligated into a pUC19 vector which is restricted with the same enzymes.

EXAMPLE 3

Sequencing of cryIC(b)

Subclone pSB204H is used to obtain the sequence to the 5' of the HincII site, and the sequence downstream of the HincII site is determined using pSB204.7. Plasmid pSB204 is used to determine the sequence through the HincII site.

Sanger Dideoxy Nucleotide Sequencing

The T7 Sequencing Kit (Pharmacia LKB) is used to determine the sequence of both strands of the cryIC(b) gene. Compression areas are resolved using the Deaza T7 Sequencing Kit (Pharmacia). Both kits are used according to the manufacturer's recommendations. A BRL sequencing apparatus is used with BRL's Bisacrylamide:acrylamide 6% gel mix to make 49 cm×35 cm×0.4 mm sequencing gels. The gels are run using a constant power output of 55 watts and 1× TBE, diluted from a 10× stock containing 121.1 g Tris base, 55 g boric acid, and 7.4 g $Na_2EDTA$, dissolved in $H_2O$ and adjusted to a final volume of 1 liter. Running times for gels are approximately 1.5 hours for short gels and 3.5 hours for longer gels.

EXAMPLE 5

Bioassay

The CryIC(b) protein is isolated from *E. coli* cells transformed with pSB204 using the following protocol. Cells are centrifuged at 10,000 rpm for 15 min, resuspended in 10 mM Tris-HCl, pH 8 and 0.25% Tween 20/Triton X-100. Cells are centrifuged as before, then resuspended (20 ml/1 broth) in 10 mM Tris-HCl, pH 8, containing 10 mM EDTA. Cells are disrupted by a French press (>20,000 lb) and centrifuged as before to collect inclusion bodies. After a saline wash, the precipitate is resuspended in water and the same volume of 1M NaCl containing 20 mM CAPS-NaOH, pH 10.5 and 2 mM EDTA. This is centrifuged as before, and the washing step is repeated twice to remove soluble proteins, then a water wash is performed. The precipitate is resuspended in 10 mM Tris-HCl, pH 8, containing 10 mM EDTA, and aliquots are frozen.

The solubilization steps are all performed over ice. 6 ml of suspension is added to 120 µl mercaptoethanol and 500 mM PMSF. 2N NaOH is added until the pH is 10.5. This is centrifuged at 15,000 rpm for 10 minutes, and column chromatography is run on the supernatant. Conditions for the chromatography are: 32×1000 mm; Sephacryl S-300 HR packing; solvent is 10 mM CAPS-NaOH, pH 10.5, 50 mM NaCl and 1 mM EDTA; speed is 90 ml/hr; monitoring is at 280 nm. 1.0 OD FS; chart speed is 0.5 mm/min; and collection is 6 in (9 ml)/tube. For acid precipitation, fractions are adjusted to pH 4.4 and incubated on ice for 1 hour, then centrifuged at 15,000 rpm for 5 min. The precipitate is dissolved in 1×TE, pH 8 and amount is estimated by measuring UV absorbance at 280 nm.

Figure 3:
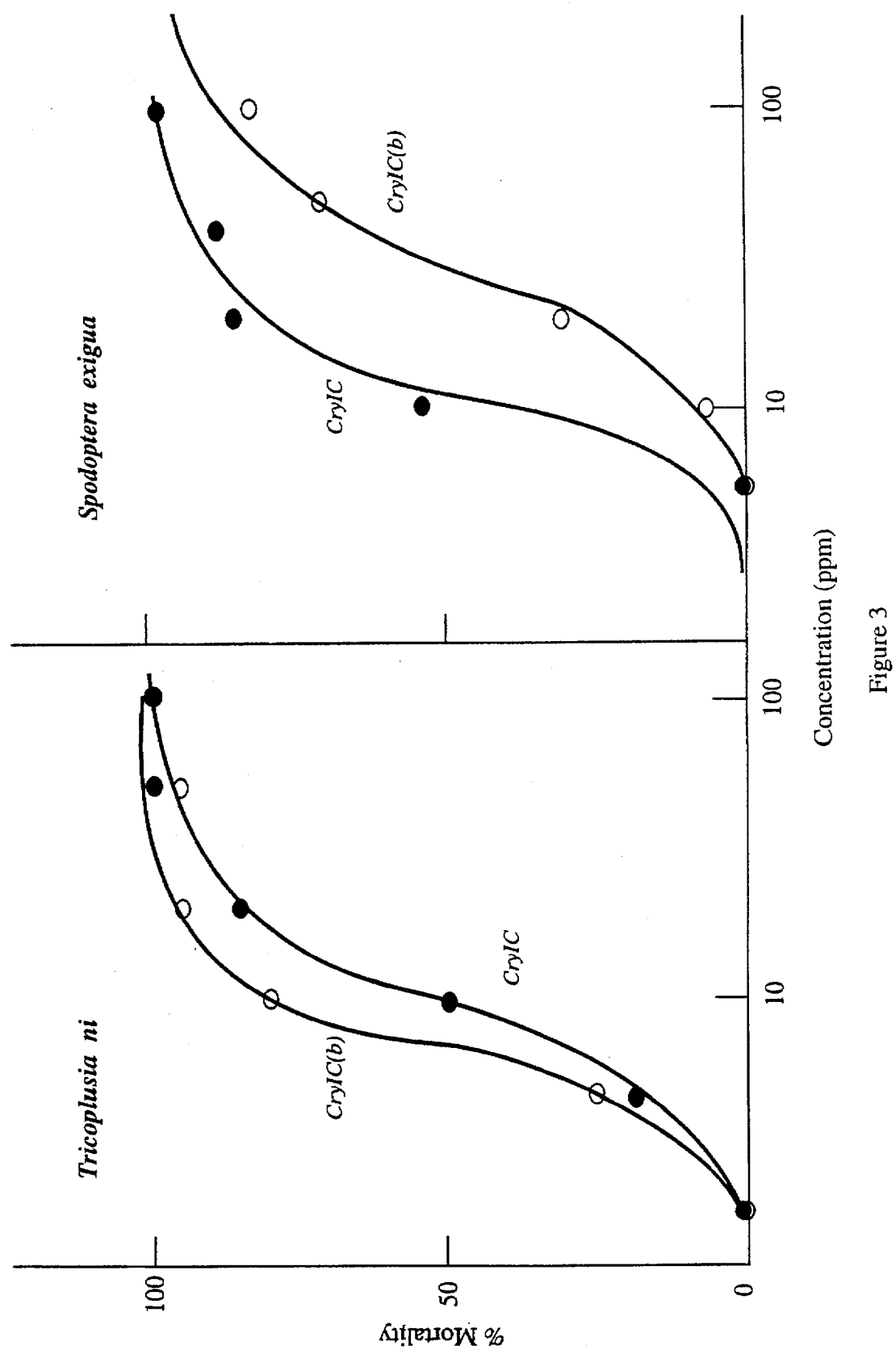
FIG. 3 shows the results of a bioassay of the CryIC(b) protein compared to CryIC in two species, *T. ni* and *S. exigua*.

10 mls of each sample is added to 90 ml of molten insect diet (52° C.) and mixed well. Insects (10 per dose per species) are infested and mortality is recorded after four days for *S. exigua* and after 3 days for *T. ni*. Results are presented in FIG. 3 which compares CryIC and CryIC(b) proteins.

TABLE 1

| SEQUENCE of CryIC(b) | |
|---|---|
| TAGATTTTAT ATAAGTATAA AAAATAATAA GACTTTAATA TAAGTTAAGG GAATACAAAT | 60 |
| CCTTAATGCA TTGGTTAAAT ATTATAAACT CTAAAGCATG GATGATGGTT GAGAAGTAAG | 120 |
| TAGATTATTA ACACCCTGGG TCTATTTTAG CCCCAGGGTA TAAATTGATA TTTAATAAAA | 180 |
| TCGGTTGCAC TTTGAGTATT TTTTCATAGA ATGACTCATA TGATTAACAT TGCAATACAG | 240 |
| TAAAAGATCT TTAGTTATAA AGAAAAACTA TTACGCTAAA AAGTGGAGGG AACAT ATG Met 1 | 298 |

| GAG AAT AAT ATT CAA AAT CAA TGC GTA CCT TAC AAT TGT TTA AGT AAT | 346 |
| Glu Asn Asn Ile Gln Asn Gln Cys Val Pro Tyr Asn Cys Leu Ser Asn | |
|     5                     10                  15                | |

| CCT GAG GAG ATA CTT TTA GAT GGA GAA AGA ATA TCA ACT GGT AAT TCA | 394 |
| Pro Glu Glu Ile Leu Leu Asp Gly Glu Arg Ile Ser Thr Gly Asn Ser | |
|         20                  25                  30              | |

| TCA ATT GAT ATC TCT CTG TCA CTT GTC CAG CTT CTG GTA TCT AAC TTT | 442 |
| Ser Ile Asp Ile Ser Leu Ser Leu Val Gln Leu Leu Val Ser Asn Phe | |
|     35                  40                  45                  | |

| GTA CCA GGG GGA GGA TTT TTA GTT GGA TTA TTA GAT TTT GTA TGG GGA | 490 |
| Val Pro Gly Gly Gly Phe Leu Val Gly Leu Leu Asp Phe Val Trp Gly | |
| 50                  55                  60                  65  | |

| ATA GTA GGC CCT TCT CCA TGG GAT GCA TTT CTA GTG CAA ATT GAA CAA | 538 |
| Ile Val Gly Pro Ser Pro Trp Asp Ala Phe Leu Val Gln Ile Glu Gln | |
|                 70                  75                  80      | |

| TTA ATT AAT GAA AGA ATA GCT GCA TAT GCT AGG TCT GCA GCA ATT TCT | 586 |
| Leu Ile Asn Glu Arg Ile Ala Ala Tyr Ala Arg Ser Ala Ala Ile Ser | |
|             85                  90                  95          | |

| AAT TTA GAA GGA TTA GGA AAC AAT TTC AAT ATA TAT GTG GAA GCA TTT | 634 |
| Asn Leu Glu Gly Leu Gly Asn Asn Phe Asn Ile Tyr Val Glu Ala Phe | |
|         100                 105                 110             | |

| AAA GAA TGG GAA GCA GAT CCT GAT AAT CCA GTA ACC AGG ACT AGA GTA | 682 |
| Lys Glu Trp Glu Ala Asp Pro Asp Asn Pro Val Thr Arg Thr Arg Val | |
|     115                 120                 125                 | |

| GGT GAT CGC TTT CGT ATA CTT GAT GGG CTA CTT GAA AGG GAC ATC CCT | 730 |
| Val Asp Arg Phe Arg Ile Leu Asp Gly Leu Leu Glu Arg Asp Ile Pro | |
| 130                 135                 140                 145 | |

| TCA TTT CGA ATT GCT GGA TTT GAA GTA CCC CTT TTA TCC GTT TAT GCT | 778 |
| Ser Phe Arg Ile Ala Gly Phe Glu Val Pro Leu Leu Ser Val Tyr Ala | |
|                 150                 155                 160     | |

| CAA GCG GCC AAT TTG CAT CTA GCT ATA TTA AGA GAT TCT TCA ATT TTT | 826 |
| Gln Ala Ala Asn Leu His Leu Ala Ile Leu Arg Asp Ser Ser Ile Phe | |
|             165                 170                 175         | |

| GGA GCA AGA TGG GGA TTG ACA ACA ATA AAT GTC AAT GAA AAC TAT AAT | 874 |
| Gly Ala Arg Trp Gly Leu Thr Thr Ile Asn Val Asn Glu Asn Tyr Asn | |
|         180                 185                 190             | |

| AGG CTA ATT AGG CAT ATT GAT GAA TAT GCT AAT CAC TGT GCA GAT ACG | 922 |
| Arg Leu Ile Arg His Ile Asp Glu Tyr Ala Asn His Cys Ala Asp Thr | |
|     195                 200                 205                 | |

TABLE 1-continued

SEQUENCE of CryIC(b)

| | | | | | | | | | | | | | | | | |
|---|---|---|---|---|---|---|---|---|---|---|---|---|---|---|---|---|
| TAT | AAT | CGG | GGA | TTA | AAT | AAT | TTA | CCA | AAA | TCT | ACG | TAT | CAA | GAT | TGG | 970 |
| Tyr 210 | Asn | Arg | Gly | Leu | Asn 215 | Asn | Leu | Pro | Lys | Ser 220 | Thr | Tyr | Gln | Asp | Trp 225 | |
| ATA | ACA | TAT | AAT | CGA | TTA | CGG | AGA | GAC | TTA | ACA | TTA | ACT | GTA | TTA | GAT | 1018 |
| Ile | Thr | Tyr | Asn | Arg 230 | Leu | Arg | Arg | Asp | Leu 235 | Thr | Lue | Thr | Val | Leu 240 | Asp | |
| ATC | GCT | GCT | TTC | TTT | CCA | AGC | TAT | GAC | AAT | AGG | AGA | TAT | CCA | ATT | CAG | 1066 |
| Ile | Ala | Ala | Phe 245 | Phe | Pro | Ser | Tyr | Asp 250 | Asn | Arg | Arg | Tyr | Pro 255 | Ile | Gln | |
| TCA | GTT | GGT | CAA | CTA | ACA | AGG | GAA | ATT | TAT | ACG | GAC | CCA | TTA | ATT | ACT | 1114 |
| Ser | Val | Gly 260 | Gln | Leu | Thr | Arg | Glu 265 | Ile | Tyr | Thr | Asp | Pro 270 | Leu | Ile | Thr | |
| TTT | AAT | CCA | CAG | TTA | CAG | TCT | GTA | GCT | CAA | TTA | CCT | ACT | TTT | AAC | GTT | 1162 |
| Phe | Asn 275 | Pro | Gln | Leu | Gln | Ser 280 | Val | Ala | Gln | Leu | Pro 285 | Thr | Phe | Asn | Val | |
| ATG | GAA | AGC | AAC | GCA | ATT | AGA | ACT | CCT | CAT | TTA | TTT | GAT | GTA | TTG | AAT | 1210 |
| Met 290 | Glu | Ser | Asn | Ala | Ile 295 | Arg | Thr | Pro | His | Leu 300 | Phe | Asp | Val | Leu | Asn 305 | |
| AAT | CTT | ACA | ATT | TTT | ACA | GAT | TGG | TTT | AGT | GTT | GGA | CGC | AAC | TTT | TAT | 1258 |
| Asn | Leu | Thr | Ile | Phe 310 | Thr | Asp | Trp | Phe | Ser 315 | Val | Gly | Arg | Asn | Phe 320 | Tyr | |
| TGG | GGA | GGA | CAT | CGA | GTA | ATA | TCT | AAC | CGT | ATA | GGA | GGA | GGT | AAC | ATA | 1306 |
| Trp | Gly | Gly | His 325 | Arg | Val | Ile | Ser | Asn 330 | Arg | Ile | Gly | Gly | Gly 335 | Asn | Ile | |
| ACA | TCT | CCT | ATA | TAT | GGA | AGA | GAG | GCG | AAT | CAG | GAG | CCT | CCA | AGA | TCT | 1354 |
| Thr | Ser | Pro 340 | Ile | Tyr | Gly | Arg | Glu 345 | Ala | Asn | Gln | Glu | Pro 350 | Pro | Arg | Ser | |
| TTT | ACT | TTT | AAT | GGG | CCT | GTT | TTT | AGG | ACT | TTA | TCA | AAT | CCT | ACT | TTT | 1402 |
| Phe | Thr 355 | Phe | Asn | Gly | Pro | Val 360 | Phe | Arg | Thr | Leu | Ser 365 | Asn | Pro | Thr | Phe | |
| AGA | CCT | TTA | CAG | CAA | CCT | TGG | CCA | GCG | CCA | CCA | TTT | AAT | TTA | CGT | GGT | 1450 |
| Arg 370 | Pro | Leu | Gln | Gln | Pro 375 | Trp | Pro | Ala | Pro | Pro 380 | Phe | Asn | Leu | Arg | Gly 385 | |
| GTT | GAA | GGA | GTA | GAA | TTT | TCT | ACA | CCT | TTA | AAT | AGC | TTT | ACG | TAT | CGA | 1498 |
| Val | Glu | Gly | Val | Glu 390 | Phe | Ser | Thr | Pro | Leu 395 | Asn | Ser | Phe | Thr | Tyr 400 | Arg | |
| GGA | AGA | GGT | ACG | GTT | GAT | TCT | TTA | ACT | GAG | TTA | CCG | CCT | GAG | GAT | AAT | 1546 |
| Gly | Arg | Gly | Thr 405 | Val | Asp | Ser | Leu | Thr 410 | Glu | Leu | Pro | Pro | Glu 415 | Asp | Asn | |
| AGT | GTG | CCT | CCT | CGC | GAA | GGA | TAT | AGT | CAT | CGT | TTA | TGT | CAT | GCA | ACT | 1594 |
| Ser | Val | Pro 420 | Pro | Arg | Glu | Gly | Tyr 425 | Ser | His | Arg | Leu | Cys 430 | His | Ala | Thr | |
| TTT | GTT | CAA | AGA | TCT | GGA | ACC | CCA | TTT | TTA | ACA | ACT | GGT | CCA | GTA | TTT | 1642 |
| Phe | Val 435 | Gln | Arg | Ser | Gly | Thr 440 | Pro | Phe | Leu | Thr | Thr 445 | Gly | Pro | Val | Phe | |
| TCT | TGG | ACG | CAT | CGT | AGT | GCT | ACT | GAT | CGA | AAT | ATA | ATC | TAC | CCG | GAT | 1690 |
| Ser 450 | Trp | Thr | His | Arg | Ser 455 | Ala | Thr | Asp | Arg | Asn 460 | Ile | Ile | Tyr | Pro | Asp 465 | |
| GTA | ATT | AAC | CAA | ATA | CCG | TTA | GTA | AAA | GCA | TTC | AAC | CTT | ACT | TCA | GGT | 1738 |
| Val | Ile | Asn | Gln | Ile 470 | Pro | Leu | Val | Lys | Ala 475 | Phe | Asn | Leu | Thr | Ser 480 | Gly | |
| ACC | TCT | GTA | GTC | AGA | GGT | CCA | GGA | TTT | ACA | GGA | GGG | GAT | ATC | ATC | CGA | 1786 |
| Thr | Ser | Val | Val 485 | Arg | Gly | Pro | Gly | Phe 490 | Thr | Gly | Gly | Asp | Ile 495 | Ile | Arg | |
| ACT | AAC | GTT | AAT | GGT | AGT | GTA | CTA | AGT | ATG | AGT | CTT | AAT | TTT | AGT | AAC | 1834 |
| Thr | Asn | Val 500 | Asn | Gly | Ser | Val | Leu 505 | Ser | Met | Ser | Leu | Asn 510 | Phe | Ser | Asn | |

TABLE 1-continued

| SEQUENCE of CryIC(b) | |
|---|---|
| ACA ACA TTA CAG CGG TAT CGT GTG AGA GTT CGT TAT GCT GCT TCT CAA<br>Thr Thr Leu Gln Arg Tyr Arg Val Arg Val Arg Tyr Ala Ala Ser Gln<br>    515                      520                        525 | 1882 |
| ACA ATG GTC ATG AGC GTA ACT GTT GGA GGG AGT ACT ACT GGT AAT CAA<br>Thr Met Val Met Ser Val Thr Val Gly Gly Ser Thr Thr Gly Asn Gln<br>530                      535                      540                      545 | 1930 |
| GGA TTC CCT AGT ACT ATG AGT GCA AAT GGG GCT TTG ACA TCT CAA TCA<br>Gly Phe Pro Ser Thr Met Ser Ala Asn Gly Ala Leu Thr Ser Gln Ser<br>                    550                      555                      560 | 1978 |
| TTT AGA TTC GCA GAA TTT CCT GTA GGT ATT AGT GCA TCT GGC AGT CAA<br>Phe Arg Phe Ala Glu Phe Pro Val Gly Ile Ser Ala Ser Gly Ser Gln<br>            565                      570                      575 | 2026 |
| GGT GCA TCA ATA AGT ATT AGT AAT AAT GTA GGT AGA CAA ATG TTT CAC<br>Gly Ala Ser Ile Ser Ile Ser Asn Asn Val Gly Arg Gln Met Phe His<br>        580                      585                      590 | 2074 |
| TTA GAT AGA ATT GAA TTT CTC CCA GTT ACT TCT ACA TTT GAG GAG GAA<br>Leu Asp Arg Ile Glu Phe Leu Pro Val Thr Ser Thr Phe Glu Glu Glu<br>    595                      600                      605 | 2122 |
| TAT GAT TTA GAA AGA GCG CAA GAG GCG GTG AAT GCC CTG TTT ACT TCT<br>Tyr Asp Leu Glu Arg Ala Gln Glu Ala Val Asn Ala Leu Phe Thr Ser<br>610                      615                      620                      625 | 2170 |
| ACG AAC CAA CTA GGG CTA AAA ACA GAT GTA ACG GAT TAT CAT ATT GAT<br>Thr Asn Gln Leu Gly Leu Lys Thr Asp Val Thr Asp Tyr His Ile Asp<br>                  630                        635                      640 | 2218 |
| CAA GTA TCA AAT CTA GTT GAA TGC TTA TCG GAT GAA TTT TGT CTG GAT<br>Gln Val Ser Asn Leu Val Glu Cys Leu Ser Asp Glu Phe Cys Leu Asp<br>        645                      650                      655 | 2266 |
| GAA AAG CGA GAA TTG TCT GAG AAA GTC AAA CAT GCG AAG CGA CTC AGC<br>Glu Lys Arg Glu Leu Ser Glu Lys Val Lys His Ala Lys Arg Leu Ser<br>        660                      665                      670 | 2314 |
| GAT GAG CGC AAT TTA CTC CAG GAT CGA AAT TTC AGA TCC ATT AAT GGG<br>Asp Glu Arg Asn Leu Leu Gln Asp Arg Asn Phe Arg Ser Ile Asn Gly<br>    675                      680                      685 | 2362 |
| CAA CTA GAC CGT GGC TGG AGA GGA AGT ACG GAT ATT ACC ATC CAA GGT<br>Gln Leu Asp Arg Gly Trp Arg Gly Ser Thr Asp Ile Thr Ile Gln Gly<br>690                      695                      700                      705 | 2410 |
| GGA GAT GAC GTA TTC AAA GAG AAT TAC GTC ACA CTG CCG GGT ACC TTT<br>Gly Asp Asp Val Phe Lys Glu Asn Tyr Val Thr Leu Pro Gly Thr Phe<br>                  710                      715                      720 | 2458 |
| GAT GAG TGC TAT CCA ACG TAT CTA TAT CAA AAA ATA GAT GAA TCG AAA<br>Asp Glu Cys Tyr Pro Thr Tyr Leu Tyr Gln Lys Ile Asp Glu Ser Lys<br>            725                      730                      735 | 2506 |
| TTA AAA TCC TAT ACA CGT TAC GAG TTA AGA GGG TAT ATC GAG GAT AGT<br>Leu Lys Ser Tyr Thr Arg Tyr Glu Leu Arg Gly Tyr Ile Glu Asp Ser<br>        740                      745                      750 | 2554 |
| CAA GAT TTA GAA ATC TAT TTG ATT CGC TAC AAT GCA AAA CAC GAA ATA<br>Gln Asp Leu Glu Ile Tyr Leu Ile Arg Tyr Asn Ala Lys His Glu Ile<br>    755                      760                      765 | 2602 |
| GTA AAT GTA CCA GGT ACA GGG AGT TTA TGG CCT CTT TCT ATA GAA AAT<br>Val Asn Val Pro Gly Thr Gly Ser Leu Trp Pro Leu Ser Ile Glu Asn<br>770                      775                      780                      785 | 2650 |
| TCA ATT GGG CCT TGT GGA GAA CCG AAT CGC TGC GCG CCA CAC CTT GAA<br>Ser Ile Gly Pro Cys Gly Glu Pro Asn Arg Cys Ala Pro His Leu Glu<br>                  790                      795                      800 | 2698 |
| TGG AAT CCT AAT CTA GAT TGT TCC TGC AGG GAC GGG GAA AAA TGT GCC<br>Trp Asn Pro Asn Leu Asp Cys Ser Cys Arg Asp Gly Glu Lys Cys Ala<br>        805                      810                      815 | 2746 |
| CAT CAT TCC CAT CAT TTC TCC TTG GAC ATT GAT GTT GGA TGT ACA GAC<br>His His Ser His His Phe Ser Leu Asp Ile Asp Val Gly Cys Thr Asp<br>        820                      825                      830 | 2794 |

TABLE 1-continued

SEQUENCE of CryIC(b)

| | | | | | | | | | | | | | | | | |
|---|---|---|---|---|---|---|---|---|---|---|---|---|---|---|---|---|
| TTA | AAT | GAG | GAC | TTA | GGT | GTA | TGG | GTG | ATC | TTC | AAG | ATT | AAG | ACG | CAA | 2842 |
| Leu | Asn 835 | Glu | Asp | Leu | Gly | Val 840 | Trp | Val | Ile | Phe | Lys 845 | Ile | Lys | Thr | Gln | |
| GAT | GGC | CAT | GCA | AGA | CTA | GGA | AAT | CTA | GAG | TTT | CTC | GAA | GAG | AAA | CCA | 2890 |
| Asp 850 | Gly | His | Ala | Arg | Leu 855 | Gly | Asn | Leu | Glu | Phe 860 | Leu | Glu | Glu | Lys | Pro 865 | |
| CTA | TTA | GGG | GAA | GCA | CTA | GCT | CGT | GTG | AAA | AGA | GCG | GAG | AAG | AAA | TGG | 2938 |
| Leu | Leu | Gly | Glu | Ala 870 | Leu | Ala | Arg | Val | Lys 875 | Arg | Ala | Glu | Lys | Lys 880 | Trp | |
| AGA | GAC | AAA | CGT | GAA | AAA | TTG | GAA | TGG | GAA | ACA | AAT | ATT | GTT | TAT | AAA | 2986 |
| Arg | Asp | Lys | Arg 885 | Glu | Lys | Leu | Glu | Trp 890 | Glu | Thr | Asn | Ile | Vla 895 | Tyr | Lys | |
| GAG | GCA | AAA | GAA | TCT | GTA | GAT | GCT | TTA | TTT | GTG | AAC | TCT | CAA | TAT | GAT | 3034 |
| Glu | Ala | Lys 900 | Glu | Ser | Val | Asp | Ala 905 | Leu | Phe | Val | Asn | Ser 910 | Gln | Tyr | Asp | |
| AGA | TTA | CAA | GCG | GAT | ACG | AAT | ATC | GCG | ATG | ATT | CAT | GCG | GCA | GAT | AAA | 3082 |
| Arg | Leu 915 | Gln | Ala | Asp | Thr | Asn 920 | Ile | Ala | Met | Ile | His 925 | Ala | Ala | Asp | Lys | |
| CGC | GTT | CAT | AGA | ATT | AGA | GAA | GCA | TAC | CTT | CCA | GAA | TTA | TCT | GTA | ATT | 3130 |
| Arg 930 | Val | His | Arg | Ile | Arg 935 | Glu | Ala | Tyr | Leu | Pro 940 | Glu | Leu | Ser | Val | Ile 945 | |
| CCG | GGT | GTA | AAT | GCG | GGC | ATT | TTC | GAA | GAA | TTA | GAG | GGA | CGC | ATT | TTC | 3178 |
| Pro | Gly | Val | Asn | Ala 950 | Gly | Ile | Phe | Glu | Glu 955 | Leu | Glu | Gly | Arg | Ile 960 | Phe | |
| ACA | GCC | TAC | TCT | CTA | TAT | GAT | GCG | AGA | AAT | GTC | ATT | AAA | AAT | GGC | GAT | 3226 |
| Thr | Ala | Tyr | Ser 965 | Leu | Tyr | Asp | Ala | Arg 970 | Asn | Val | Ile | Lys | Asn 975 | Gly | Asp | |
| TTC | AAT | AAT | GGT | TTA | TTA | TGC | TGG | AAC | TTG | AAA | GGG | CAT | GTA | GAT | GTA | 3274 |
| Phe | Asn | Asn 980 | Gly | Leu | Leu | Cys | Trp 985 | Asn | Leu | Lys | Gly | His 990 | Val | Asp | Val | |
| GAA | GAA | CAA | AAC | AAC | CAT | CGT | TCA | GTC | CTT | GTT | GTC | CCG | GAA | TGG | GAA | 3322 |
| Glu | Glu 995 | Gln | Asn | Asn | His | Arg 1000 | Ser | Val | Leu | Val | Val 1005 | Pro | Glu | Trp | Glu | |
| GCA | GAG | GTG | TCC | CAA | GAA | GTT | CGT | GTC | TGT | CCA | GGT | CGT | GGC | TAT | ATC | 3370 |
| Ala 1010 | Glu | Val | Ser | Gln | Glu 1015 | Val | Arg | Val | Cys | Pro 1020 | Gly | Arg | Gly | Tyr | Ile 1025 | |
| CTT | CGT | GTT | ACA | GCG | TAC | AAA | GAG | GGA | TAT | GGA | GAG | GGC | TGC | GTA | ACC | 3418 |
| Leu | Arg | Val | Thr | Ala 1030 | Tyr | Lys | Glu | Gly | Tyr 1035 | Gly | Glu | Gly | Cys | Val 1040 | Thr | |
| ATT | CAT | GAG | ATC | GAA | GAC | AAT | ACA | GAC | GAA | CTG | AAA | TTT | AGC | AAC | TGT | 3466 |
| Ile | His | Glu | Ile 1045 | Glu | Asp | Asn | Thr | Asp 1050 | Glu | Leu | Lys | Phe | Ser 1055 | Asn | Cys | |
| GTT | GAA | GAG | GAA | GTA | TAT | CCA | AAC | AAC | ACG | GTA | ACG | TGT | AAT | GAT | TAT | 3514 |
| Val | Glu | Glu 1060 | Glu | Val | Tyr | Pro | Asn | Asn 1065 | Thr | Val | Thr | Cys | Asn 1070 | Asp | Tyr | |
| ACT | GCG | ACT | CAA | GAA | GAA | TAC | GGG | GGT | GCG | TAC | ACT | TCC | CGT | AAT | CAT | 3562 |
| Thr | Ala 1075 | Thr | Gln | Glu | Glu | Tyr 1080 | Gly | Gly | Ala | Tyr | Thr 1085 | Ser | Arg | Asn | His | |
| GGA | TAT | GGC | AAA | TCT | TAT | GAA | AGT | AAT | TCT | TCC | GTA | CAA | GCT | GAT | TAT | 3610 |
| Gly 1090 | Tyr | Gly | Lys | Ser | Tyr 1095 | Glu | Ser | Asn | Ser | Ser 1100 | Val | Gln | Ala | Asp | Tyr 1105 | |
| GCG | TCA | GTT | TAT | GAA | GAA | AAA | GCG | GAC | ACA | GAT | GGA | CGA | AGA | GAT | AAT | 3658 |
| Ala | Ser | Val | Tyr | Glu 1110 | Glu | Lys | Ala | Asp | Thr 1115 | Asp | Gly | Arg | Arg | Asp 1120 | Asn | |
| CAT | TGC | GAA | TCT | AAC | AGA | GGG | TAT | GGG | GAT | TAC | ACG | CCA | CTA | CCA | GCT | 3706 |
| His | Cys | Glu | Ser 1125 | Asn | Arg | Gly | Tyr | Gly 1130 | Asp | Tyr | Thr | Pro | Leu 1135 | Pro | Ala | |

TABLE 1-continued

SEQUENCE of CryIC(b)

| | | | | | | | | | | | | | | |
|---|---|---|---|---|---|---|---|---|---|---|---|---|---|---|
| GGT | TAT | GTA | ACA | AAA | GAA | TTA | GAA | TAC | TTC | CCA | GAA | ACC | GAT | AAG | GTA | 3754
| Gly | Tyr | Val | Thr | Lys | Glu | Leu | Glu | Tyr | Phe | Pro | Glu | Thr | Asp | Lys | Val |
| | | 1140 | | | | | 1145 | | | | | 1150 | | | |
| TGG | GTT | GAG | ATT | GGA | GAA | ACG | GAA | GGA | ACA | TTC | ATT | GTG | GAT | AGT | GTG | 3802
| Trp | Val | Glu | Ile | Gly | Glu | Thr | Glu | Gly | Thr | Phe | Ile | Val | Asp | Ser | Val |
| | 1155 | | | | | 1160 | | | | | 1165 | | | | |
| GAA | TTA | CTC | CTT | ATG | GAG | GAA | TAAGGTATGT | TTTAAAATGT | AGCGTGTGCA | | | | | | | 3853
| Glu | Leu | Leu | Leu | Met | Glu | Glu | | | | | | | | | |
| 1170 | | | | | 1175 | | | | | | | | | | |

AATAAAGAAT GTTTACTGAC CAGTATTAAC AGATAAATAA GAAACTTCTA TATAAATAAA   3913

AAACGGACAT CAATCTTAAG AGAATGATGT CCGTTTTTTG TATGATTTGA TTCAACGAGT   3973

GATATGTAAA TATATTTTTT TGCGAAGTCT TTACATAACA AAAAAATTCG TATAGCAAAA   4033

TTCTAAATTT AACCTTAAAT ATAGTTAGGG TGAAAATATG CCAAACTAAT TTATTCCGAA   4093

TGTTAATTCG AAA   4106

---

What is claimed is:

1. A method of controlling insects comprising exposing the insects to an insecticidal composition comprising an insecticidally effective amount of a polypeptide characterized by having the amino acid sequence of SEQ ID No. 2 and an agriculturally acceptable carrier thereof.

2. The method of claim 1 wherein the insect is a spodopteran.

3. A method of controlling insects comprising exposing the insects to an insecticidally effective amount of a protein derived from expression of a vector in a cell, wherein said vector comprises a promoter operably linked to a nucleic acid having a sequence encoding the amino acid sequence of SEQ ID NO:2.

4. The method of claim 3 wherein the insect is a spodopteran.

5. A method of controlling insects comprising exposing the insects to an insecticidal composition comprising an insecticidally effective amount of a polypeptide characterized by having the amino acid sequence of residues 451 to 650 inclusive of SEQ ID NO. 2 and an agriculturally acceptable carrier thereof.

6. The method of claim 5 wherein the insect is a spodopteran.

7. A method of controlling insects comprising exposing the insects to an insecticidally effective amount of a protein derived from expression of a vector in a cell, wherein said vector comprises a promoter operably linked to a nucleic acid having a sequence encoding a truncated CryIC(b) toxin polypeptide which comprises an amino acid sequence which results after an insect ingests and cleaves the polypeptide of SEQ ID NO:2.

8. The method of claim 7 wherein the insect is a spodopteran.

* * * * *